United States Patent
Solomon et al.

(10) Patent No.: US 8,647,326 B2
(45) Date of Patent: Feb. 11, 2014

(54) SYSTEM FOR CLEANING LUER CONNECTORS

(75) Inventors: Donald D. Solomon, North Salt Lake, UT (US); F. Mark Ferguson, Salt Lake City, UT (US); Robert Hitchcock, Sandy, UT (US); Steven Bandis, West Jordan, UT (US); James Mercer, West Jordan, UT (US); Michael Howlett, Salt Lake City, UT (US)

(73) Assignee: Catheter Connections, Inc., Salt Lake City, UT (US)

( * ) Notice: Subject to any disclaimer, the term of this patent is extended or adjusted under 35 U.S.C. 154(b) by 762 days.

(21) Appl. No.: 12/610,033

(22) Filed: Oct. 30, 2009

(65) Prior Publication Data

US 2010/0047123 A1 Feb. 25, 2010

Related U.S. Application Data

(63) Continuation-in-part of application No. 12/171,997, filed on Jul. 11, 2008, now Pat. No. 8,197,749, which is a continuation-in-part of application No. 12/164,310, filed on Jun. 30, 2008, now Pat. No. 8,177,761, which is a continuation-in-part of application No. 12/014,388, filed on Jan. 15, 2008, now abandoned.

(60) Provisional application No. 60/880,541, filed on Jan. 16, 2007.

(51) Int. Cl.
*A61M 5/00* (2006.01)

(52) U.S. Cl.
USPC ........... 604/533; 604/535; 604/256; 604/265; 422/28; 422/292

(58) Field of Classification Search
USPC .............. 422/28, 292; 604/29, 256, 265, 533, 604/539, 905
See application file for complete search history.

(56) References Cited

U.S. PATENT DOCUMENTS

| 1,744,026 A | 1/1930 | Baltzley |
| 2,351,804 A | 6/1944 | Jerome |
| 3,431,548 A | 3/1969 | Le Roy Busler |
| 3,446,596 A | 5/1969 | Salivar et al. |
| 3,987,930 A | 10/1976 | Fuson |

(Continued)

FOREIGN PATENT DOCUMENTS

| WO | WO 2006099306 | 9/2006 |
| WO | WO-2008/089196 | 7/2008 |

(Continued)

OTHER PUBLICATIONS

Restriction Requirement mailed Nov. 13, 2008 in U.S. Appl. No. 12/014,388, now abandoned.

(Continued)

*Primary Examiner* — Sean E Conley
(74) *Attorney, Agent, or Firm* — Sunstein Kann Murphy & Timber LLP

(57) ABSTRACT

One or more caps can be used to cover and sterilize one or more separated medical connectors. A pair of caps can be connected to each other and sealed when in a pre-use state. The paired caps can be unsealed so as to permit connection to the medical connectors.

16 Claims, 24 Drawing Sheets

(56) References Cited

U.S. PATENT DOCUMENTS

| | | | |
|---|---|---|---|
| 4,232,677 A | 11/1980 | Leibinsohn | |
| 4,324,239 A | 4/1982 | Gordon et al. | |
| 4,340,052 A | 7/1982 | Dennehey et al. | |
| 4,346,703 A | 8/1982 | Dennehey et al. | |
| 4,354,490 A | 10/1982 | Rogers | |
| 4,369,781 A | 1/1983 | Gilson et al. | |
| 4,402,691 A | 9/1983 | Rosenthal et al. | |
| 4,432,764 A | 2/1984 | Lopez | |
| 4,432,766 A | 2/1984 | Bellotti et al. | |
| 4,440,207 A | 4/1984 | Genatempo et al. | |
| 4,450,624 A | 5/1984 | Collier | |
| 4,572,373 A | 2/1986 | Johansson | 206/515 |
| 4,671,306 A | 6/1987 | Spector | 132/73 |
| 4,778,447 A | 10/1988 | Velde et al. | |
| 4,838,875 A | 6/1989 | Somor | |
| 5,205,821 A | 4/1993 | Kruger et al. | |
| 5,242,425 A | 9/1993 | White et al. | |
| 5,445,270 A | 8/1995 | Dratz | 206/443 |
| 5,466,219 A | 11/1995 | Lynn et al. | |
| 5,554,135 A | 9/1996 | Menyhay | |
| 5,694,978 A | 12/1997 | Heilmann et al. | |
| 5,702,017 A | 12/1997 | Goncalves | 220/23.4 |
| 5,792,120 A | 8/1998 | Menyhay | |
| 5,894,015 A | 4/1999 | Rechtin | |
| 5,951,519 A | 9/1999 | Utterberg | |
| 5,954,957 A | 9/1999 | Chin-Loy et al. | 210/232 |
| 6,045,539 A | 4/2000 | Menyhay | |
| 6,171,287 B1 | 1/2001 | Lynn et al. | |
| 6,523,686 B1 | 2/2003 | Bae | 206/315.9 |
| 6,932,795 B2 | 8/2005 | Lopez et al. | |
| 6,960,191 B2 | 11/2005 | Howlett et al. | |
| 7,040,598 B2 | 5/2006 | Raybuck | |
| 7,198,611 B2 | 4/2007 | Connell et al. | |
| D547,446 S | 7/2007 | Racz et al. | |
| D550,355 S | 9/2007 | Racz et al. | |
| 7,282,186 B2 | 10/2007 | Lake, Jr. et al. | 422/300 |
| 7,316,669 B2 | 1/2008 | Ranalletta | |
| D607,325 S | 1/2010 | Rogers et al. | |
| 7,762,524 B2 | 7/2010 | Cawthon et al. | |
| 7,780,794 B2 | 8/2010 | Rogers et al. | 134/6 |
| 7,922,701 B2 | 4/2011 | Buchman | 604/256 |
| 7,985,302 B2 | 7/2011 | Rogers et al. | |
| 2002/0093192 A1 | 7/2002 | Matkovich | |
| 2003/0140441 A1 | 7/2003 | Stafford | |
| 2003/0153865 A1 | 8/2003 | Connell et al. | |
| 2003/0198502 A1 | 10/2003 | Maloney et al. | |
| 2004/0039341 A1 | 2/2004 | Ranalletta | 604/199 |
| 2004/0195136 A1 | 10/2004 | Young et al. | 206/484 |
| 2004/0201216 A1 | 10/2004 | Segal et al. | |
| 2004/0214316 A1 | 10/2004 | O'Connell | |
| 2004/0258560 A1 | 12/2004 | Lake, Jr. et al. | 422/28 |
| 2005/0033267 A1 | 2/2005 | Decaria | |
| 2005/0124970 A1 | 6/2005 | Kunin et al. | |
| 2005/0147524 A1 | 7/2005 | Bousquet | 422/28 |
| 2005/0203460 A1 | 9/2005 | Kim | |
| 2005/0245883 A1 | 11/2005 | Baldwin | |
| 2005/0266714 A1 | 12/2005 | Higgins et al. | |
| 2006/0030827 A1 | 2/2006 | Raulerson et al. | |
| 2007/0112333 A1 | 5/2007 | Hoang et al. | 604/533 |
| 2007/0202177 A1 | 8/2007 | Hoang | |
| 2007/0282280 A1* | 12/2007 | Tennican | 604/246 |
| 2007/0287989 A1 | 12/2007 | Crawford et al. | |
| 2007/0293818 A1 | 12/2007 | Stout et al. | |
| 2007/0293822 A1 | 12/2007 | Crawford et al. | |
| 2008/0019889 A1 | 1/2008 | Rogers et al. | 422/292 |
| 2008/0021381 A1 | 1/2008 | Lurvey et al. | |
| 2008/0027399 A1 | 1/2008 | Harding et al. | |
| 2008/0038167 A1 | 2/2008 | Lynn | |
| 2008/0039803 A1 | 2/2008 | Lynn | |
| 2008/0086091 A1 | 4/2008 | Anderson et al. | |
| 2008/0095680 A1 | 4/2008 | Steffens et al. | |
| 2008/0105704 A1 | 5/2008 | Pritchard | |
| 2008/0107564 A1 | 5/2008 | Sternberg et al. | |
| 2008/0132880 A1 | 6/2008 | Buchman | |
| 2008/0147047 A1 | 6/2008 | Davis et al. | |
| 2008/0177250 A1 | 7/2008 | Howlett et al. | |
| 2008/0235888 A1 | 10/2008 | Vaillancourt et al. | |
| 2009/0008393 A1 | 1/2009 | Howlett et al. | |
| 2009/0062766 A1 | 3/2009 | Howlett et al. | |
| 2009/0205151 A1 | 8/2009 | Fisher et al. | |
| 2010/0049170 A1 | 2/2010 | Solomon et al. | |
| 2010/0242993 A1 | 9/2010 | Hoang et al. | |
| 2010/0306938 A1 | 12/2010 | Rogers et al. | |
| 2010/0313366 A1 | 12/2010 | Rogers et al. | |
| 2011/0044850 A1 | 2/2011 | Solomon et al. | 422/28 |
| 2011/0213341 A1 | 9/2011 | Solomon et al. | |
| 2011/0217212 A1 | 9/2011 | Solomon et al. | |

FOREIGN PATENT DOCUMENTS

| | | |
|---|---|---|
| WO | WO-2008/100950 | 8/2008 |
| WO | WO-2010/002808 | 1/2010 |
| WO | WO-2010/141508 | 12/2010 |
| WO | WO-2011/053924 | 5/2011 |
| WO | WO-2011/066565 | 6/2011 |
| WO | WO-2011/066586 | 6/2011 |

OTHER PUBLICATIONS

Amendment and Response to Restriction Requirement filed Mar. 24, 3009 in U.S. Appl. No. 12/014,388, now abandoned.

Interview Summary mailed Sep. 1, 2009 in U.S. Appl. No. 12/014,388, now abandoned.

Office Action mailed May 5, 2009 in U.S. Appl. No. 12/014,388, now abandoned.

Amendment and Response to Office Action filed Sep. 4, 2009 in U.S. Appl. No. 12/014,388, now abandoned.

Notice of Non-Compliance Amendment mailed Sep. 28, 2009 in U.S. Appl. No. 12/014,388, now abandoned.

Amendment and Response to Office Action filed Oct. 2, 2009 in U.S. Appl. No. 12/014,388, now abandoned.

Final Office Action mailed Jan. 27, 2010 in U.S. Appl. No. 12/014,388, now abandoned.

RCE and Amendment and Response to Office Action filed Apr. 26, 2010 in U.S. Appl. No. 12/014,388, now abandoned.

Office Action mailed Jun. 21, 2010 in U.S. Appl. No. 12/014,388, now abandoned.

Amendment and Response to Office Action filed Oct. 19, 2010 in U.S. Appl. No. 12/014,388, now abandoned.

Interview Summary mailed Oct. 25, 2010 in U.S. Appl. No. 12/014,388, now abandoned.

Final Office Action mailed Dec. 23, 2010 in U.S. Appl. No. 12/014,388, now abandoned.

Express Abandonment filed Feb. 15, 2011 in U.S. Appl. No. 12/014,388, now abandoned.

Restriction Requirement mailed May 21, 2010 in co-pending U.S. Appl. No. 12/164,310, now published as US 2009/0008393.

Amendment and Response to Restriction Requirement filed Jun. 21, 2010 in co-pending U.S. Appl. No. 12/164,310, now published as US 2009/0008393.

Office Action mailed Aug. 16, 2010 in co-pending U.S. Appl. No. 12/164,310, now published as US 2009/0008393.

Amendment and Response to Office Action filed Oct. 29, 2010 in co-pending U.S. Appl. No. 12/164,310, now published as US 2009/0008393.

Interview Summary mailed Oct. 25, 2010 in co-pending U.S. Appl. No. 12/164,310, now published as US 2009/0008393.

Notice of Non-Compliant Amendment mailed Nov. 3, 2010 in co-pending U.S. Appl. No. 12/164,310, now published as US 2009/0008393.

Amendment and Response to Office Action filed Feb. 16, 2011 in co-pending U.S. Appl. No. 12/164,310, now published as US 2009/0008393.

Preliminary Amendment filed Dec. 7, 2010 in co-pending U.S. Appl. No. 12/171,997, now published as US 2009/0062766.

Restriction Requirement mailed Dec. 9, 2010 in co-pending U.S. Appl. No. 12/171,997, now published as US 2009/0062766.

(56) References Cited

OTHER PUBLICATIONS

Notification of Transmittal of the International Search Report and the Written Opinion of the International Searching Authority issued Aug. 1, 2008 in International Application No. PCT/US2008/051087.
Notification of Transmittal of the International Search Report and the Written Opinion of the International Searching Authority issued Jan. 6, 2011 in International Application No. PCT/US2010/054995.
Notification of Transmittal of the International Search Report and the Written Opinion of the International Searching Authority issued Jan. 26, 2011 in International Application No. PCT/US2010/058404.
Notification of Transmittal of the International Search Report and the Written Opinion of the International Searching Authority issued Feb. 7, 2011 in International Application No. PCT/US2010/058453.
Co-pending U.S. Appl. No. 12/917,336 titled Disinfecting Caps and Systems and Associated Methods, filed Nov. 1, 2010.
Co-pending Design U.S. Appl. No. 29/383,403 titled Capping System for Use With One or More Medical Connectors, filed Jan. 17, 2011.
Co-pending U.S. Appl. No. 12/956,704 titled Disinfecting Caps Having an Extendable Feature and Related Systems and Methods, filed Nov. 30, 2010.
Co-pending U.S. Appl. No. 12/957,263 titled Disinfecting Caps Having Sealing Features and Related Systems and Methods, filed Nov. 30, 2010.
Response to Office Action dated Sep. 4, 2009 for U.S. Appl. No. 12/014,388.
Office Action dated May 5, 2009 for U.S. Appl. No. 12/014,388.
Response to Restriction Election dated Feb. 13, 2009 for U.S. Appl. No. 12/014,388.
Office Action dated Nov. 13, 2008 for U.S. Appl. No. 12/014,388.
International Search Report with Written Opinion for International Application No. PCT/US2009/049094.
Buchman, et al., "A New Central Venous Catheter Cap: Decreased Microbial Growth and Risk for Catheter-Related Bloodstream Infection." The Journal of Vascular Access 2009, 10: pp. 11-21.
Cures Port Protector product brochure, circa Nov. 2008, 2 pages, available at http://www.iveramed.com/docsCuros%20Brochure-FINAL.pdf.
Hospira Male/Female Sterile Cap product packaging insert and brochure, circa Aug. 2004, 2 pages.
BD Q-Syte Luer Access Split Septum product brochure, circa Nov. 2008, 4 pages, available at http://www.bd.com/infusion/pdfs/D16333.pdf.
Tego Connector product brochure, circa Nov. 2008 2 pages, available at http://www.icumed.com/Docs-Tego/M1-1148%20TEGO%20Folder%20Brochure%20Rev.3.pdf.

Baxa Corporation Launches PadLock Set Saver for IV Safety press release, Oct. 10, 2007, 2 pages, available at http://www.pr.com/press-release/55432.
Baxa Corporation PatLock Set Saver Specifications and Instructions for Use, copyright 2007, 2 pages, available at http://www.baxa.com/resources/docs/5300103905C.pdf.
Baxa Corporation PadLock product brochure, copyright 2007, 1 page, available at http://www.baxa.com/resources/docs/5300104405A.pdf.
Baxa Corporation PadLock Microbial Testing Technical Paper, copyright 2007, 4 pages, available at http://www.baxa.com/resources/docs/technicalPaters.PadLockMicrobialChallengeTechPaper.pdf.
Baxa Corporation PatLock catalog page, 3 pages, copyright 2009, available at http://www.baxa.com/SearchResults/ProductDetail/?id=6452BFB9-3048-7B87-701697FB93902BA6.
One Less Problem, Managing Infection Control, Jun. 2008, available at http://www.baxa.com/resources/docs/OneLessProbPaper.pdf.
Unomedical Medical Products catalog, circa Jan. 2006, 2 pages, available at http://www.unomedical.net/au/section05/section10/LocalSSI/..%5C..%5Cpdf%5Cmedical.pdf.
Braun product catalog, circa Aug. 2008, 2 pages.
Curos Port Protector web page from http://iveramed.com dated Jul. 11, 2008, 1 page.
Notice of Publication of U.S. Appl. No. 12/610,141 dated Feb. 25, 2010.
Office Action dated Jan. 27, 2010 for U.S. Appl. No. 12/014,388.
Response to Office Action dated Apr. 26, 2010 for U.S. Appl. No. 12/014,388.
International Search Report and Written Opinion for PCT/US2009/049094 dated Aug. 31, 2009.
Final Office Action mailed Apr. 22, 2011 in co-pending U.S. Appl. No. 12/164,310, now published as U.S. Publication No. US-2009/0008393.
Response to Requirement for Election of Species filed Apr. 1, 2011 in co-pending U.S. Appl. No. 12/171,997, now published as U.S. Publication No. US-2009/0062766.
Office Action mailed Jun. 9, 2011 in co-pending U.S. Appl. No. 12/171,997, now published as U.S. Publication No. US-2009/0062766.
Preliminary Amendment filed Jun. 13, 2011 in co-pending U.S. Appl. No. 29/383,403.
Preliminary Amendment filed May 13, 2011 in co-pending U.S. Appl. No. 12/956,704.
Preliminary Amendment filed May 13, 2011 in co-pending U.S. Appl. No. 12/957,263.
Maki, Dennis G., "In Vitro Studies of a Novel Antimicrobial Luer-Activated Needleless Connector for Prevention of Catheter-Related Blookstream Infection," Clinical Infection Diseases, Jun. 15, 2010, vol. 50, Issue 12, pp. 1580-1587.

* cited by examiner

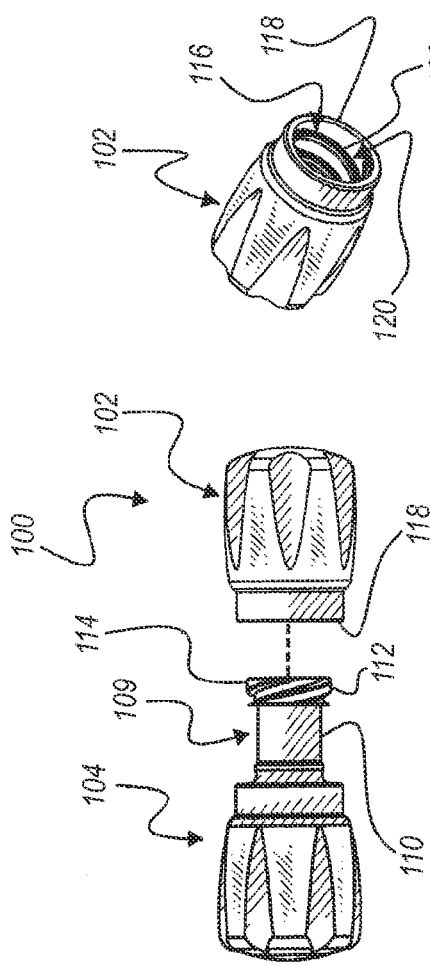
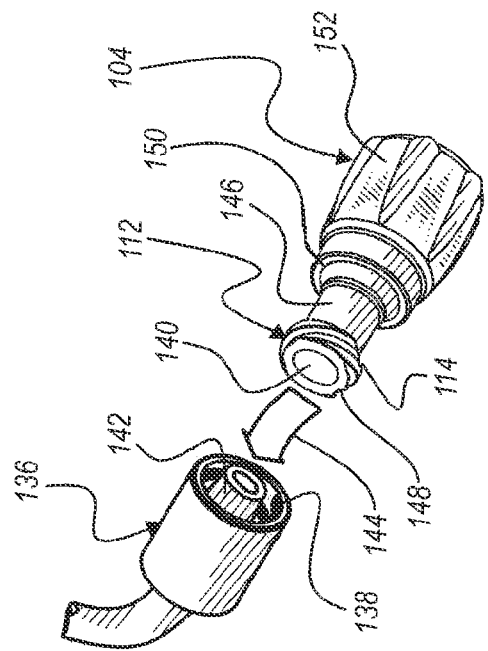
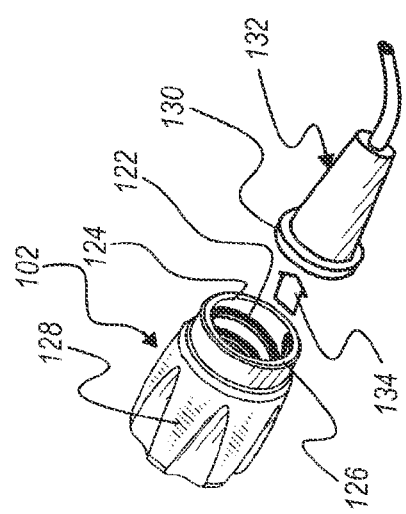

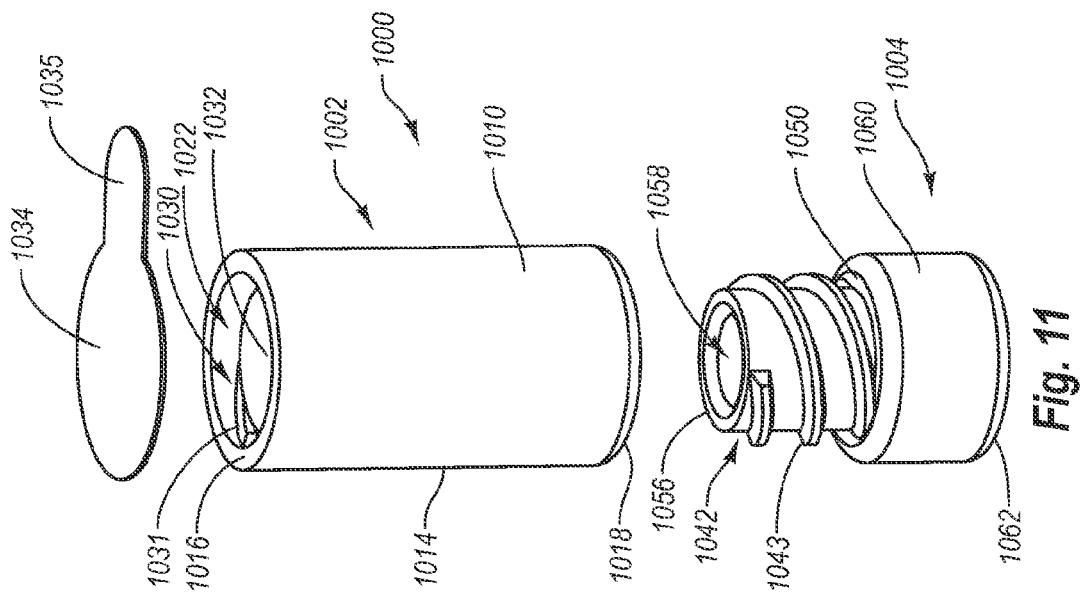
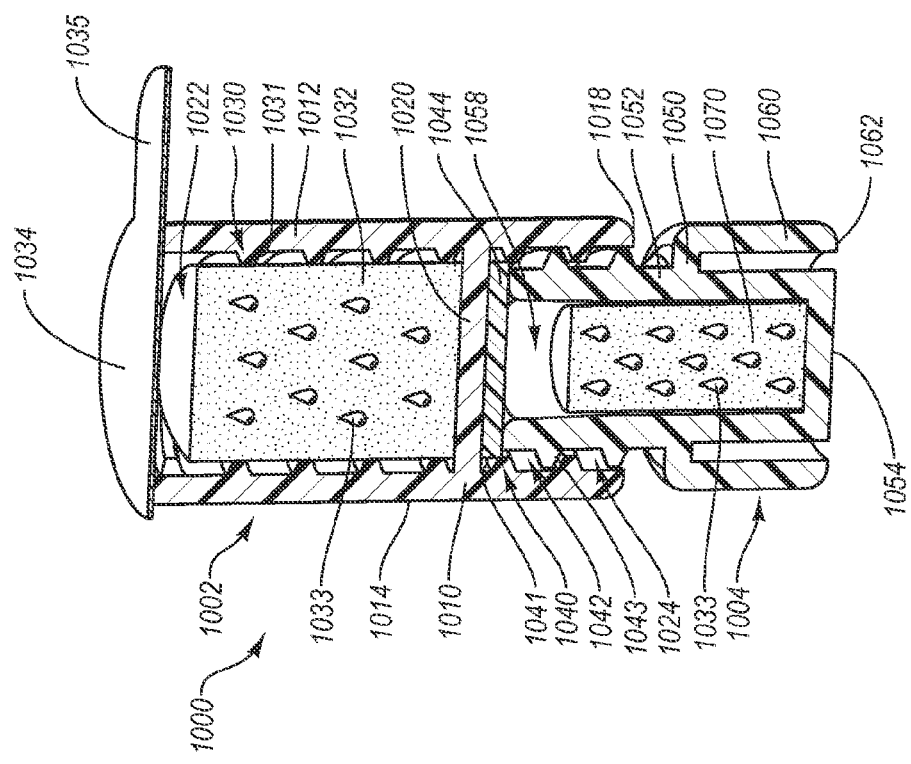

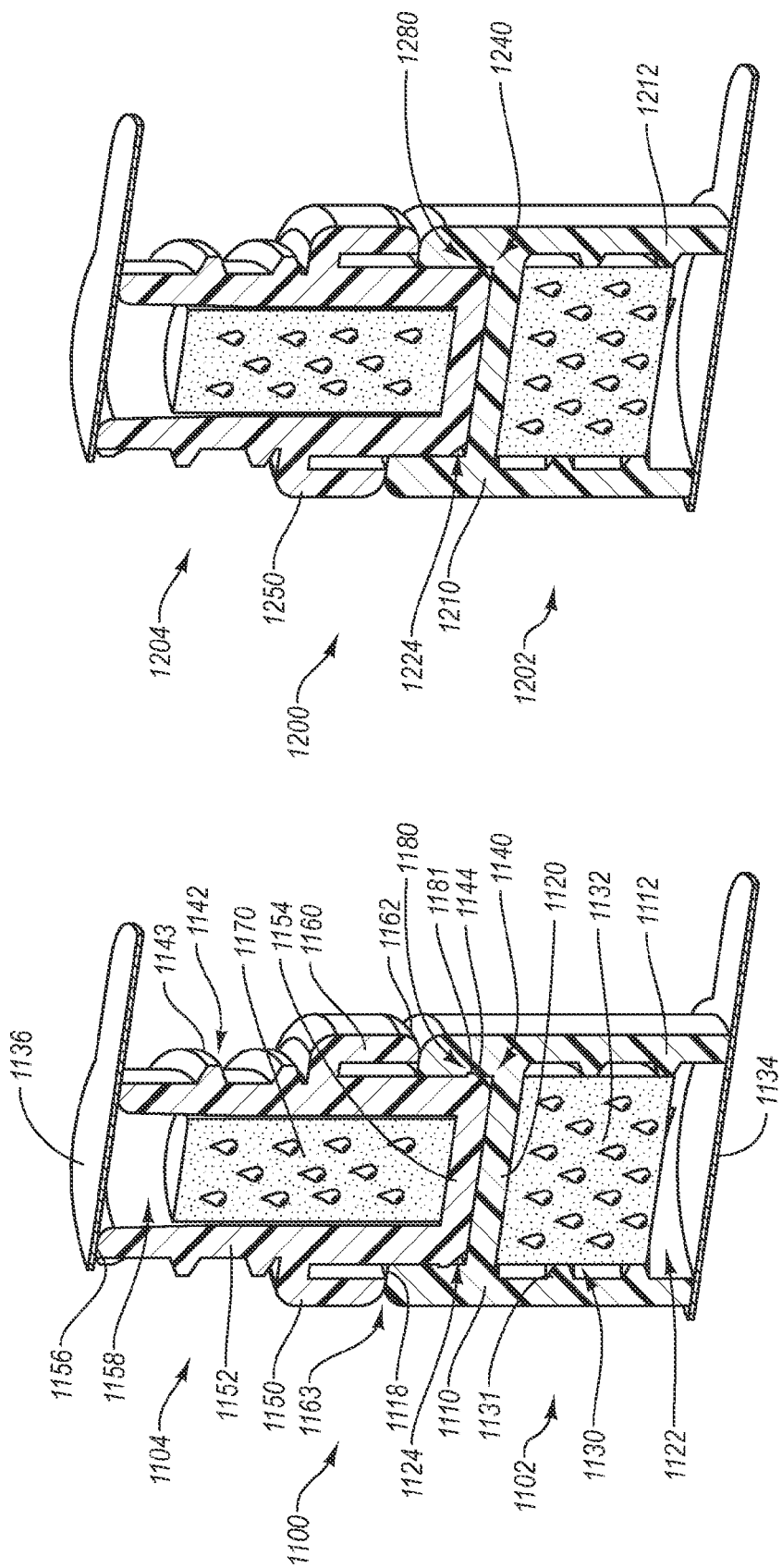

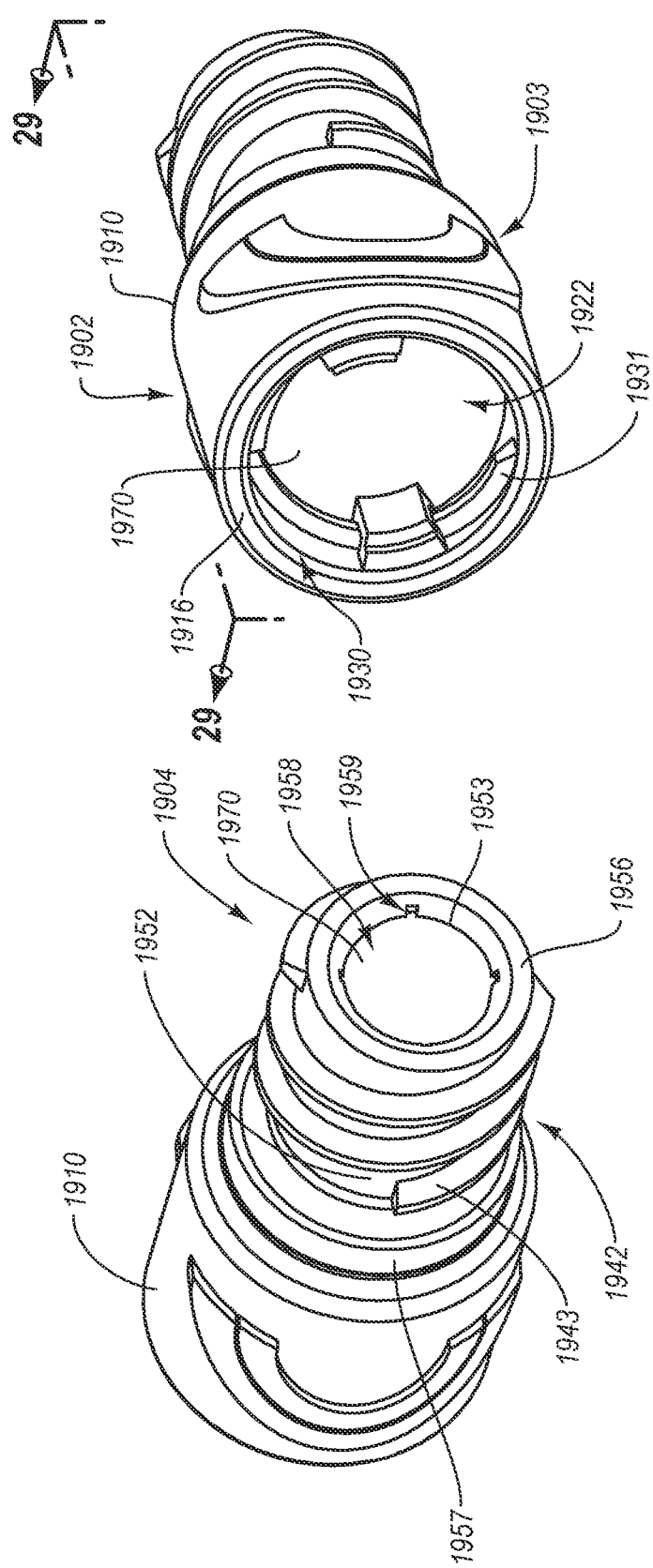

SYSTEM FOR CLEANING LUER CONNECTORS

CROSS-REFERENCE TO RELATED APPLICATIONS

This application is a continuation-in-part of U.S. patent application Ser. No. 12/171,997, titled STERILITY-PROTECTING CAPS WITH FLUID RESERVOIR FOR SEPARATED CONNECTORS, filed Jul. 11, 2008, which is a continuation-in-part of U.S. patent application Ser. No. 12/164,310, titled NESTABLE STERILITY-PROTECTING CAPS WITH FLUID RESERVOIR FOR SEPARATED CONNECTORS, filed Jun. 30, 2008, which is a continuation-in-part of U.S. patent application Ser. No. 12/014,388, titled NESTABLE STERILITY-PROTECTING CAPS FOR SEPARATED CONNECTORS, filed Jan. 15, 2008, which claims the benefit of U.S. Provisional Application No. 60/880,541, titled ANTISEPTIC PROTECTIVE CAP FOR MALE AND FEMALE SCREW-TOGETHER CONNECTORS, filed Jan. 16, 2007, the entire contents of each of which are hereby incorporated by reference herein.

BACKGROUND

1. Technical Field

The present disclosure generally relates to caps for medical connectors and more specifically relates to caps that can be used to protect the sterility of unconnected medical connectors, such as connectors that may be used for fluid flow or for fluid delivery systems.

2. Related Art

Bloodstream infections, such as may be caused by microorganisms that enter patients via intravascular catheters, are a significant cause of illness and excess medical costs. A substantial number of such infections occur in U.S. intensive care units annually. Additionally, a significant fraction of these infections result in death.

Guidelines from the Centers for Disease Control and Prevention describe various ways to limit bloodstream infections in hospital, outpatient, and home care settings. The guidelines address issues such as hand hygiene, catheter site care and admixture preparation. However, despite these guidelines, such infections continue to plague healthcare systems at relatively unchanged rates.

Impregnating catheters with various antimicrobial agents is one approach for reducing these infections. Impregnated catheters, however, provide less than satisfactory results. Additionally, some microbes have developed resistance to the various antimicrobial agents used in the catheters. Other systems and approaches have also been developed, but these likewise suffer from a variety of limitations and drawbacks.

SUMMARY

Disclosed herein are sterility caps, and related systems and methods, that can reduce the threat of microorganisms entering the bloodstream of a patient via fluid flow or fluid delivery systems, such as, for example, needleless injection sites and/or fluid transfer devices having a male luer. In some embodiments, a cap is configured to couple with and sterilize a medical connector having a male luer. In some embodiments, a pair of caps are attached to each other when in a pre-use state, and each cap can be coupled with a separate medical connector. In further embodiments, the caps can be separated from each other and individually secured to complementary components of a medical fluid flow or fluid delivery system. Other or further features of various embodiments are also disclosed and are set forth in the appended claims, which are hereby incorporated by reference in this summary section.

BRIEF DESCRIPTION OF THE DRAWINGS

FIG. 2 is an exploded perspective view of the medical caps of FIG. 1;

FIG. 3 is a perspective view of a first of the medical caps of FIG. 1, which shows internal threads;

FIG. 4 is a perspective view of the cap of FIG. 3 and an associated medical connector about to be connected therewith;

FIG. 5 is a perspective view of a second of the caps of FIG. 1 and a luer lock connector to which the male cap may be affixed;

FIG. 10 is a cross-sectional perspective view of another embodiment of an assembly that includes a pair of caps, which are attached to each other via a threaded interface;

FIG. 11 is an exploded perspective view of the assembly of FIG. 10 showing the caps detached from each other;

FIG. 12 is a cross-sectional perspective view of another embodiment of an assembly that includes a pair of caps, which are attached to each other via a snapping interface;

FIG. 13 is a cross-sectional perspective view of another embodiment of an assembly that includes a pair of caps, which are attached to each other via a friction-fit interface;

FIG. 27 is a perspective view focusing on one cap portion of the assembly of FIG. 25, with covers removed from the assembly;

FIG. 28 is a perspective view focusing on the other cap portion of the assembly of FIG. 25, with covers removed from the assembly;

DETAILED DESCRIPTION

Disclosed herein are caps that can be used to protect and/or sterilize medical connectors when the connectors are separated (e.g., temporarily separated) from each other. Systems and methods related to such caps are also disclosed. An example of medical connectors for which caps disclosed herein may be used are intravascular connectors associated with a fluid pathway, such as a central line. Commonly, a fluid pathway is used to intermittently administer medications to a patient. For example, a fluid pathway, which communicates fluids with a patient's blood stream, may have one or more connectors associated therewith. Each of the fluid pathway connectors can be connected to other connectors, such as a connector associated with an IV bag. In such a situation, the medical connectors, such as luer lock connectors, are connected and disconnected at various times, and may remain disconnected for several minutes or hours. Medical connector caps are used to cover and protect the various medical connectors while the connectors are separated from one another. When the medical connectors are separated from each other, there are two connectors that each can benefit from being covered by a cap. Therefore, in some cases, it can be advantageous to have a single connector set that can be used to provide protection for both ends of a separated connection.

Figure 1:
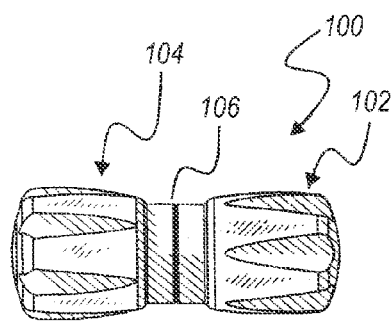
FIG. 1 is a side elevation view of an embodiment of an assembly that includes an attached pair of medical caps.
Figure 1A:
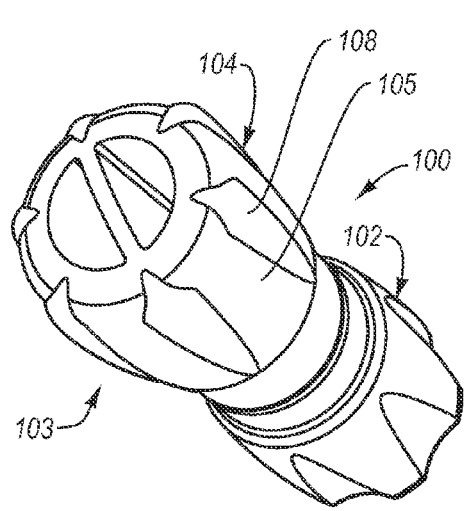
FIG. 1A is an end perspective view of the caps of FIG. 1.
Figure 1B:
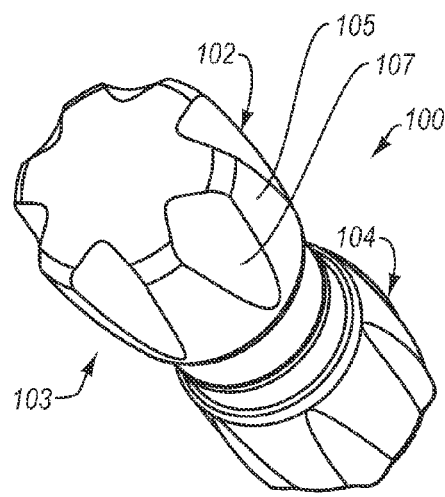
FIG. 1B is an end perspective view of the caps of FIG. 1 shown from a vantage point opposite of that shown in FIG. 1A.

Shown in FIGS. 1-1B, is a system, unit, or assembly 100 of a pair of separable caps 102 and 104, which are securely, but releasably, affixed one to the other across a common interface 106. Internal parts and surfaces of the assembly 100 are sterile and are able to reduce, prevent, or eliminate contamination of connectors with which caps 102, 104 can be coupled.

As further discussed below, in various embodiments, caps 102 and 104 can be distributed in a coupled state, such as that shown in FIGS. 1-1B, and may be decoupled by a user (e.g., a medical professional) and subsequently coupled with connectors. Caps 102 and 104 can include features to aid in such a decoupling action and/or in the coupling of caps 102, 104 with the respective connectors. For example, in the illustrated embodiment, each cap 102, 104 includes gripping features 103.

The gripping features 103 can comprise longitudinally extending lands or ridges 105 that taper from a relatively wide width near the interface 106 of the caps 102, 104 to a narrower width at or near an outer end of the cap 102, 104. The gripping features 103 can further include longitudinally extending depressions or grooves 107 between adjacent ridges 105. For example, as can be seen in FIGS. 1-8B, the grooves 107 can extend radially inwardly from an outer surface of the cap 102 that comprises the ridges 105, and the grooves 107 can also commence at a position near the interface 106 and can grow wider and deeper toward an outer end of the cap 102. The gripping features 103 can further include longitudinally extending bumps or protrusions 108 between adjacent ridges 105. As can be seen in FIGS. 1-8B, the protrusions 108 can extend radially outwardly from an outer surface of the cap 104 that comprises the ridges 105, and the protrusions 108 can also commence at a position near the interface 106 and can grow wider and taller toward an outer end of the cap 104. The uneven surfaces provided by the ridges 105 and the grooves 107 or protrusions 108 can facilitate rotational movement of the caps 102, 104 (e.g., rotational movement relative to each other), which can aid in decoupling the caps 102, 104 from each other and/or securing the caps 102, 104 to separated connectors. For example, the uneven surfaces may be easily gripped by the fingertips of a medical practitioner.

As can be seen, for example, in FIGS. 1A and 1B, the patterns of the ridges 105, grooves 107, and/or protrusions 108 can be different for the caps 102, 104. In the illustrated embodiment, cap 102 includes only ridges 105 and grooves 107, whereas cap 104 includes only ridges 105 and protrusions 108. Such differences can aid in distinguishing the caps 102, 104 from each other. Other features and methods for distinguishing the caps 102, 104 from each other are discussed further below.

Caps 102 and 104 are shown as separated from each other, or in a decoupled state, in FIG. 2, wherein cap 104 is shown as having an insertable or male section 109. Section 109 has an elongated portion 110 that ends at an exteriorly disposed threaded segment 112. Threaded segment 112 comprises threads 114 that are sized and shaped to be inserted and joined by threading into cap 102.

Cap 102, as shown in FIG. 3, has a closed, hollow interior 116, which may also be referred to as a sterilization cavity or chamber, which opens outwardly at a proximal end 118 to expose an interiorly disposed threaded segment 120 that includes threads 122. Threads 122 are of a size and pitch to complementarily engage threads 114 of cap 104 for a screw or push-on tight fit with cap 104.

As illustrated in FIG. 4, cap 102 has an interior surface 124, an opening edge 126 and an exterior surface 128, opening edge 126 being a common link between interior surface 124 and exterior surface 128. Further, threads 122 also have a size and pitch to engage a threadable segment 130 of a female connector, such as for example, female luer connector 132. Such connectors are generally and commonly used as catheter and other fluid-tight protective connectors in medical applications. As seen in FIG. 4, cap 102 provides a protective cover for connector 132 when encased about connector 132 (displaced in direction of arrow 134) whereupon threadable segment 130 engages and is drawn into a secure, but releasable connection with threads 122 of cap 102.

In some embodiments, the connector 132 comprises a needleless injection site, which may sometimes referred to as a needleless injection port, hub, valve, or device, or as a needleless access site, port, hub, valve, or device, and which can include such brands as, for example, Clave® (available from ICU Medical, Inc.), SmartSite® (available from Cardinal Health, Inc.), and Q-Syte™ (available from Becton, Dickinson and Company). Stated otherwise, in some embodiments, cap 102 can be suitably connected with any of a variety of different needless injection sites, such as those previously listed. In certain embodiments, once cap 102 has been applied to or coupled with connector 132, it is unnecessary to disinfect (e.g. treat with an alcohol swab) the connector 132 prior to each reconnection of the connector 132 with another connector, as the connector 132 will be kept in an uncontaminated state while coupled with the cap 102. Use of the cap 102 thus can replace the standard swabbing protocol.

As seen in FIG. 5, threads 114 of cap 104 are of a size and pitch to engage threads 138 of a male luer-lock connector 136. For example, connector 136 can comprise the end of an IV tubing set that is disconnected from an IV catheter needleless injection site. Note that cap 104 has a medially disposed, elongated hole 140, which may also be referred to as a sterilization chamber, into which a frustoconical luer 142 of connector 136 may be facilely and securely inserted when cap 104 is displaced in the direction of arrow 144 to engage connector 136.

Cap 104 also has a surface 146 which continues through to a circular edge 148. Further, distally displaced from circular edge 148, surface 146 abruptly ends at a circular ring shaped edge 150, which is therefrom joined to an outside surface 152. It may be noted that opening edge 126 (see FIG. 4) and ring shaped edge 150 combine to form common interface 106 (see FIG. 1) when cap 102 is affixed to cap 104 to construct assembly 100. It should also be noted that, in certain embodiments, surfaces of assembly 100, which contact internal surfaces of a connector, such as connector 132 or connector 136, are sufficiently sterile to not contaminate the inner surfaces thereof.

Internal portions and associated edges of caps 102 and 104 can be pre-sterilized and so maintained until use. Caps 102 and 104 may be injection molded using polypropylene or other material that can be sterilized and which is impervious to contaminating agents while cap 102 is nested with cap 104, before being opened for use. Caps 102 and 104 can also be impregnated or coated with an antimicrobial substance. As an example, each cap 102 and cap 104 may be individually sterilized by ethylene oxide (ETO) before final assembly and aseptically paired, or assembly 100 may be finally consolidated as a single unit and then sterilized, such as by radiation (e.g. gamma). Even so, assembly 100 should be kept intact until time for use, with internal surfaces of nested parts 102 and 104 remaining clean and sterile until assembly 100 is opened for use.

Figure 6:
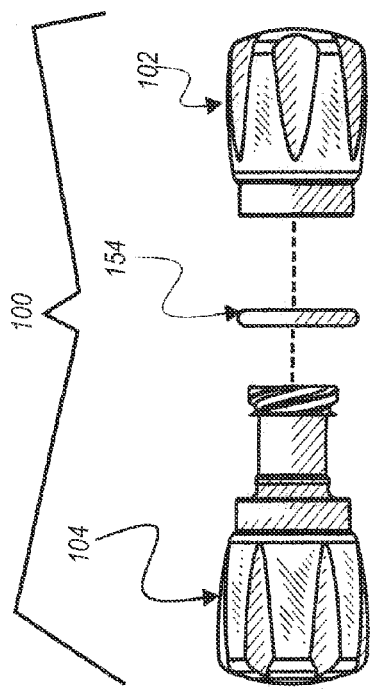
FIG. 6 is a side elevation view of an attached pair of medical caps, similar to the caps of FIG. 1, but having an embodiment of a sealing mechanism disposed about connecting edges of the caps.
Figure 7:
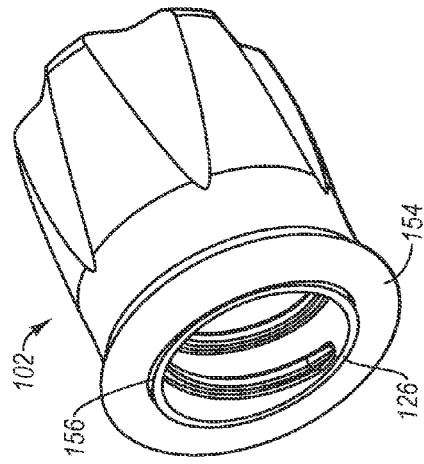
FIG. 7 is an exploded side elevation view of the cap assembly of FIG. 6.
Figure 7A:
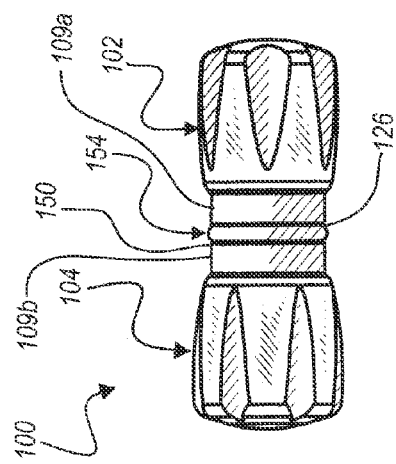
FIG. 7A is a perspective view of one of the caps of FIG. 7 with a sealing mechanism disposed thereon.
Figure 7B:
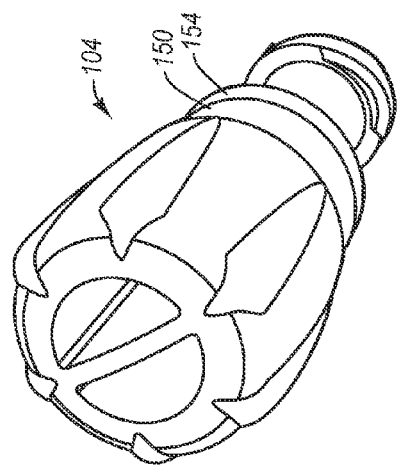
FIG. 7B is a perspective view of the other cap of FIG. 7 with a sealing mechanism disposed thereon.

Reference is now made to FIGS. 6 through 7B, wherein a seal, such as an "O" ring, is disposed between surfaces 126 and 150 to provide yet another barrier against internal surface contamination of caps 102 and 104. As seen in FIG. 6, an "O" ring 154 is disposed between surfaces 126 and 150 to provide a seal thereby. While "O" ring 154 can be displaced from caps 102 and 104 as illustrated in FIG. 7, it is anticipated that "O" ring 154 can be adapted to remain affixed to one of caps 102 and 104. For example, as illustrated in FIG. 7A, "O" ring 154 can remain positioned adjacent surface 150 on cap 104 when caps 102 and 104 are disconnected from one another, rather than being separated when cap 104 is displaced from cap 102, as seen in FIG. 7.

Alternatively, "O" ring 154 can be associated with cap 102, as seen in FIG. 7B. In particular, opening edge 126 of cap 102 can have an annular groove 156 for receiving "O" ring 154 therein. Annular groove 156 can be sized and shaped such that "O" ring 154 sealingly engages cap 104 or a medical connector when cap 102 is coupled thereto. It will be appreciated that annular groove 156 can be disposed in opening edge 126 toward the exterior of cap 102 as illustrated in FIG. 7B, or annular groove 126 can be disposed in opening edge 126 towards the interior of cap 102. In some exemplary embodiments, opening edge 126 of cap 102 does not have annular groove 126 therein. In such embodiments, "O" ring 154 can be mounted directly to opening edge 126. "O" ring 154 can be mounted on or to caps 102 or 104 in any suitable manner, including with the use of an adhesive, such as glue, a mechanical fastener, or a friction fitting.

While the seal between caps 102 and 104 has been described as being an "O" ring mounted on one of caps 102 or 104, it will be appreciated that other seals are contemplated. For example, each of caps 102 and 104 can have an "O" ring mounted thereon. In such a configuration, the two "O" rings abut each other when caps 102 and 104 are coupled together, thereby forming a seal to antiseptically partition the internal and external surfaces of caps 102 and 104. In an alternate embodiment, an "O" ring or other sealing mechanism can be mounted on surfaces 109a and 109b. Alternatively, one or both of caps 102 and 104 can be formed with a lip, bump, or groove that provides a sealing function when caps 102 and 104 are coupled to each other or to separated medical connectors. In one exemplary embodiment, one of caps 102 and 104 has a ridge extending around its interfacing surface, and the other cap has a corresponding groove in its interfacing surface into which the ridge is received to create the seal. In yet another exemplary embodiment, one or both of caps 102 and 104 can be overmolded or comolded using any known and suitable overmolding or comolding process. For example, one or both of caps 102 and 104, and associated surfaces 126 and 150, can be overmolded or comolded. Thus, caps 102 and 104 can be formed of a polymer, and surfaces 126 and 150 can be formed of a softer polymer that is comolded or overmolded to the rest of caps 102 or 104. Surfaces 126 and 150, formed of the softer polymer, are thus able to be compressed or deformed sufficiently to create an impermeable seal when caps 102 and 104 are coupled together or coupled to separated medical connectors.

As noted elsewhere herein, a sealing mechanism, as described herein, can be used to limit or prevent evaporation or loss of an antiseptic agent disposed within caps 102 and 104 when caps 102 and 104 are coupled together. Additionally, a sealing mechanism, as described herein, can also limit or prevent evaporation or loss of an antiseptic agent disposed within caps 102 and 104 when caps 102 and 104 are coupled to separated medical connectors. Further, a sealing mechanism, as described herein, can also limit or prevent microbial ingress within caps 102 and 104 when they are coupled to each other, or within caps 102 and 104 when caps 102 and 104 are individually coupled to separated medical connectors. Moreover, a sealing mechanism, as described herein, can be adapted to maintain an antiseptic agent within caps 102 and 104 when caps 102 and 104 are either coupled to one another or to separated medical connectors for a predetermined amount of time. Thus, the seal may be adapted to limit or prevent microbial ingress while also partially or completely preventing evaporation of an antiseptic agent disposed within caps 102 and 104 when caps 102 and 104 are coupled together or when caps 102 and 104 are coupled to separated medical connectors. Similarly, the seal may be adapted to limit or prevent microbial ingress while not preventing evaporation of an antiseptic agent disposed within caps 102 and 104. In yet other embodiments, no seal is provided between caps 102 and 104 when coupled together or between caps 102 and 104 when coupled to separated medical connectors.

Figure 8B:
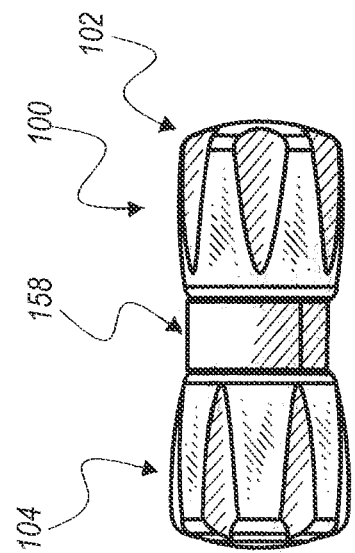
FIG. 8B is a side elevation view of the interconnected cap assembly of FIG. 8A with the seal fully in place.
Figure 8A:
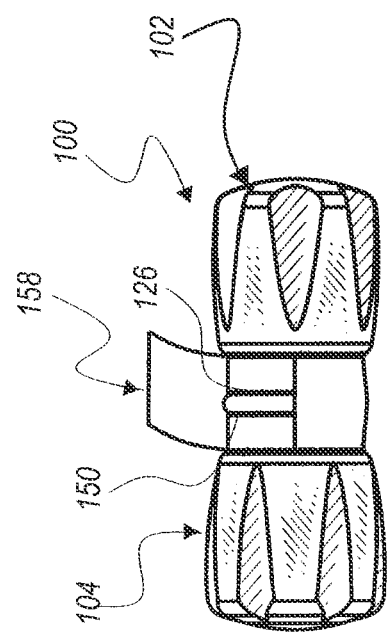
FIG. 8A is a side elevation view of the interconnected cap assembly of FIG. 6 with an embodiment of a seal partially displaced about connecting edges of the cap assembly.

Further safety in sealing against internal surface contamination may be provided by a sealing tape, or a planar or foil seal, such as tape 158 seen in FIG. 8A. Tape 158 is disposed to fully cover exposed edges of surfaces 126 and 150. Tape 158 may, for example, be of an impervious pliable material, such as a metallized-surface mylar. As seen in FIG. 8B, tape 158 is wrapped about surfaces 126 and 150 to provide a secure seal. It is preferred that tape 158 frangibly divides when cap 102 is separated from cap 104 to facilitate separation of caps 102 and 104 and provide a visible indication that the seal is broken. Thus tape 158 provides both a seal to prevent microbial ingress and a mechanism for maintaining the secure connection between caps 102 and 104 prior to use. It will be appreciated, however, that any suitable sealing mechanism can be used to maintain the secure connection between caps 102 and 104 prior to use. For example, any sealing mechanism can be used that securely and selectively couples caps 102 and 104 together, requires deliberate action to break the seal, and provides a visual indication of whether the seal has been broken. By way of example and not limitation, a suitable sealing mechanism may include a heat stake, a frictional seal, a barbed seal, a ratchet seal, and the like.

Figure 9C:
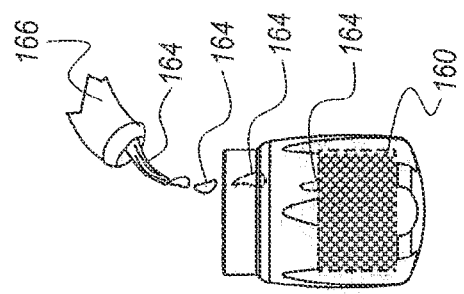
FIG. 9C is a side elevation view of the cap portion and pad of FIG. 9B with a quantity of antiseptic material being dispensed into the cap and pad.

When capping disconnected medical connectors, it can be desirable to do more than merely cover the connectors. For example, an absorbent pad, such as pad 160, seen in FIG. 9A, may be included within cap 102 (e.g., within the sterilization chamber 116), such as by displacing pad 160 into cap 102 as indicated by arrow 162. Pad 160 is seen disposed in cap 102 in FIG. 9B. An antiseptic 164 can also be disposed within cap 102 as illustrated in FIG. 9C. Antiseptic 164 can be in liquid or solid form. For example, alcohol or another stable liquid antiseptic may be added from a container 166 to be received within, wet, soak, or saturate pad 160 to a predetermined concentration level. Note that once assembly 100 is fully assembled, pad 160 will substantially remain at the predetermined concentration level due to the exterior seals provided for assembly 100 as described herein. Alternatively, or additionally, pad 160 may receive or be impregnated with a dry antiseptic, such as, for example, chlorhexidine gluconate.

Figure 9E:
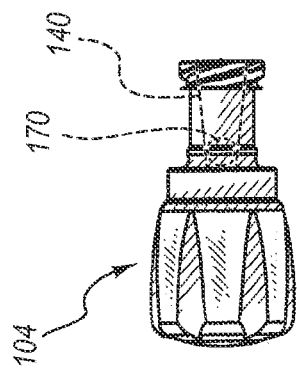
FIG. 9E is a side elevation view of the cap portion of FIG. 5 and an absorbent pad disposed therein.
Figure 9B:
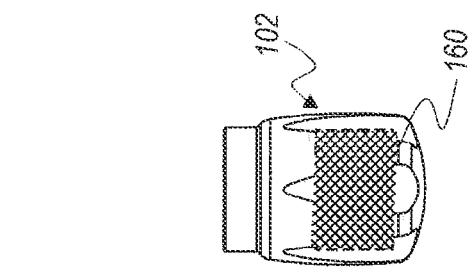
FIG. 9B is a side elevation view of the cap portion and pad of FIG. 9A schematically showing the absorbent pad disposed within the cap portion.
Figure 9A:
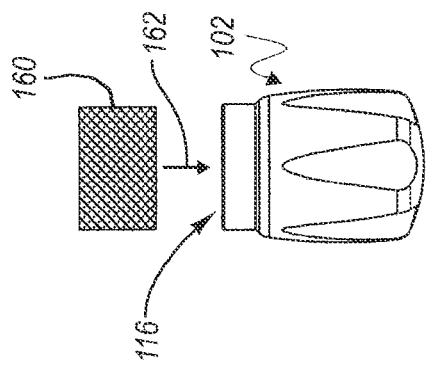
FIG. 9A is a side elevation view of the cap portion of FIG. 3 and an absorbent pad positioned above the cap portion.
Figure 9D:
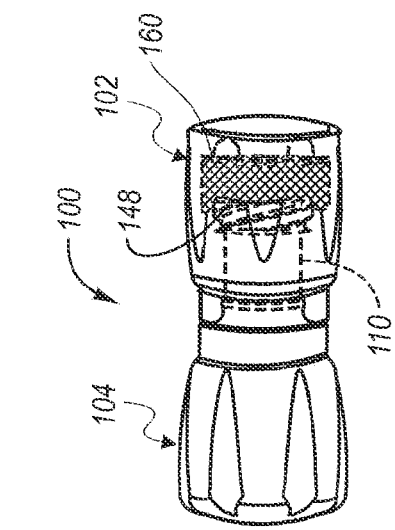
FIG. 9D is a perspective view of the cap portion containing the pad of FIGS. 9B and 9C affixed to an associated complementary cap.

Further note that once cap 104 is securely affixed to cap 102, as seen in FIG. 9D, pad 160 is disposed to contact at least circular edge 148 (see also FIG. 5). (In FIG. 9D, parts of cap 104 which are internal to assembly 100 are seen with hidden or dashed lines.) Such contact provides a wiping action preferred to make contact with a surface before contact is made with an associated connector. Note also that residual antiseptic on associated internal surfaces of cap 104 may be transferred to related parts of the associated connector for cleaning and/or disinfecting purposes.

Pad 160 can be formed of a deformable, resilient material such that when cap 104 is coupled to cap 102, elongated portion 110 can compress pad 160 within cap 102, as illustrated in FIG. 9D. Further, pad 160 can expand to its original shape when cap 104 is removed from cap 102. Similarly, pad 160 can be compressed within cap 102 when cap 102 is coupled to a medical connector, such as medical connector 132. More specifically, during the connection of cap 102 to a medical connector, cap 102 and pad 160 rotate relative to an opening edge of the medical connector, thereby drawing the medical connector into cap 102. The rotation of cap 102 causes pad 160 to wipe or scrub the opening edge of the medical connector. Pad 160 and any antiseptic disposed within cap 102 can thus cleanse and disinfect the opening edges of the medical connector. Pad 160 can also be formed such that when a medical connector is coupled to cap 102, pad 160 is deformed such that pad 160 extends around the opening edges and/or threads of the medical connector. For example, pad 160 can be formed such that as cap 102 is twisted onto medical connector 132, pad 160 deforms around threads 130 and/or the opening edges of medical connector 132, thereby scrubbing threads 130 and/or the opening edge of medical connector 132.

Pad 160 can also provide additional functionality when a liquid antiseptic is disposed within cap 102. In particular, pad 160 acts as a sponge to absorb or release the liquid antiseptic within cap 104. More specifically, when pad 160 is compressed by elongate portion 110 of cap 104 (FIG. 9D; see also elongate portion 268 compressing pad 160 in FIG. 14) or the opening edges of a medical connector coupled to cap 102, pad 160 releases at least a portion of the antiseptic so that the antiseptic can be transferred to elongate portion 110 or the opening edges of the medical connector. Conversely, when cap 102 or a medical connector is disconnected from cap 102, pad 160 expands and absorbs excess antiseptic so that the antiseptic does not drip or spill out of cap 102.

Similar to pad 160 and antiseptic 164 disposed within cap 102, cap 104 may also have a pad and/or an antiseptic disposed therein. For example, as illustrated in FIG. 9E, a pad 170 may be disposed within elongate hole 140 of cap 104. An antiseptic can also be disposed within cap 104 in a manner similar to antiseptic 164 in cap 102. Antiseptic can be in liquid or solid form. For example, alcohol or another stable liquid antiseptic may be added from a container to saturate pad 170 to a predetermined level. Alternatively, or additionally, pad 170 may be impregnated with a dry antiseptic, such as chlorhexidine gluconate. Once assembly 100 is fully assembled, an antiseptically saturated pad 170 disposed within cap 104 will substantially remain at the predetermined saturation level due to the exterior seals for assembly 100 as described above. Once caps 102 and 104 are disconnected from each other and connected to individual medical connectors, pad 170 disposed within cap 104 may scrub related parts of the associated connector for cleaning and/or disinfecting purposes. It will be appreciated, however, that in some embodiments, pad 170 may not contact a medical connector coupled to cap 104. Additionally, the antiseptic disposed within cap 104 may be transferred to the related parts of the associated medical connector for cleaning and/or disinfecting purposes.

Additional embodiments of caps such as the caps 102, 104 are provided in FIGS. 10-29 and the associated written description of U.S. patent application Ser. No. 12/171,997, titled STERILITY-PROTECTING CAPS WITH FLUID RESERVOIR FOR SEPARATED CONNECTORS, which was filed on Jul. 11, 2008 and was published as U.S. Patent Application Publication No. 2009/0062766 on Mar. 5, 2009 ("the Publication"), which is hereby incorporated by reference herein. As indicated in the Publication, any suitable feature of the illustrative embodiments of FIGS. 16-29 of the Publication, which are described with respect to a female-type cap similar to the cap 102, may be applied to or incorporated within a male-type cap, similar to the cap 104. Likewise, the female-type caps described with reference to FIGS. 16-29 of the Publication can be coupled to a male-type cap in a manner similar to that described with reference to caps 102 and 104, in which the caps 102, 104 are nested with each other. In other embodiments, any suitable feature of the caps described with respect to FIGS. 1-29 of the Publication, whether of a male or female variety, can be formed and/or employed without being nested or otherwise associated with a complementary cap.

Discussed hereafter are additional embodiments of caps, which can have coupling arrangements and/or other features that differ in certain respects from those of the caps 102, 104 described above and other caps described in the Publication. Any suitable feature of such caps can be incorporated into the caps described hereafter, and vice versa.

FIGS. 10 and 11 depict a system or assembly 1000 that includes a first protective medical connector, shield, or cap 1002 and a second protective medical connector, shield, or cap 1004. As shown in FIG. 10, the caps 1002, 1004 are connected to each other when the assembly 1000 is in a shipping or pre-use state. As shown in FIG. 11, the caps 1002, 1004 can be separated from each other such that each may be coupled with a corresponding or complementary medical connector. For example, as with the cap 102, the cap 1002 can be configured to couple with a female connector, such as a female luer lock or a needleless injection site (see, e.g., FIG. 4). Accordingly, the cap 1002 may be referred to as a female cap. As with the cap 104, the cap 1004 can be configured to couple with a male connector, such as a male luer lock (see, e.g., FIG. 5). Accordingly, the cap 1004 and may be referred to as a male cap.

With continued reference to FIGS. 10 and 11, the cap 1002 can comprise a housing 1010. The housing 1010 can be elongated, and may define a cylinder or any other suitable shape. For example, in the illustrated embodiment, the housing 1010 includes a sidewall 1012 that defines a substantially cylindrical outer surface 1014. The outer surface can be smooth, as shown, which can enhance comfort to a patient if the cap 1002 contacts the patient when coupled with a medical connector. In other embodiments, the outer surface can include gripping features, which can aid in rotating the cap 1002 relative to the cap 1004 to permit separation of the caps 1002, 1004 and/or aid in rotating the cap 1002 relative to a medical connector. Such gripping features can include, for example, ridges, grooves, and/or protrusions similar to the ridges 105, grooves 107, and protrusions 108 described above and/or an elastomeric or other coating or layer having a relatively high coefficient of friction. The sidewall 1012 can define a sealing surface 1016 at one end thereof and can define a terminal edge 1018 at an opposite end thereof.

The housing 1010 can further include a transverse wall or partition 1020. In the illustrated embodiment, the partition 1020 defines a plane that is substantially perpendicular to a longitudinal axis of the sidewall 1012. A first portion of the sidewall 1012 can cooperate with one side of the partition 1020 to define a sterilization chamber 1022, which is closed at one end by the partition 1020 and open at an opposite end thereof (e.g., the sealing surface 1016 can define an open end of the sterilization chamber 1022). Similarly, a second portion of the sidewall 1012 can cooperate with an opposite side of the partition 1020 to define a coupling chamber 1024, which likewise is closed at one end by the partition 1020 and open at an opposite end thereof (e.g., the terminal edge 1018 can define an open end of the coupling chamber 1024).

An interior surface the sidewall 1012 can include a connection interface 1030 in the region of the sterilization chamber 1022. The connection interface 1030 can comprise inwardly projecting threads 1031 similar to the threads 122 described above, and can be configured to complementarily engage a connection interface of a medical connector, such as, for example, outwardly projecting threads of a needleless injection site. The threaded connection interface 1030 thus can allow for selective coupling of the cap 1002 to a medical connector in a secure, yet selectively removable fashion. Other configurations of the connection interface 1030 may permit the cap 1002 to be coupled with a medical connector in a secure, yet selectively removable fashion, such as friction-fit, snap-fit, or other suitable interfacing arrangements.

The sterilization chamber 1022 can include a pad 1032 therein. The pad 1032 can resemble the pads 160, 170 described above. In various embodiments, the pad 1032 can be deformable, and can also be configured to retain an antiseptic 1033, such as, for example, the antiseptic 164 described above. In further embodiments, the pad 1032 can be resiliently deformable. For example, the pad 1032 can comprise any suitable sponge-like material, such as an elastomeric foam, any open-cell foam, felt, or non-woven fiber matrix, and can be configured to conform to the contours of a portion of a medical connector that is introduced into the sterilization chamber 1022 (e.g., uneven surfaces of an end of a needleless injection site; see also FIGS. 32-34 and the associated written description herein). The pad 1032 can also comprise any closed-cell foam, as well as a solid elastomeric foam such as Silicon or the like.

The pad 1032 can have a series or network of openings or spaces therein that can retain the antiseptic 1033 when the pad 1032 is in an expanded state. For example, the antiseptic 1033 can be received within, occupy, fill (or partially fill), wet, soak, or saturate at least a fraction of the pad 1032, or stated otherwise, can fill the pad 1032 to a given concentration level. Compression of the pad 1032 can cause antiseptic 1033 to egress from the pad 1032 so as to contact the medical connector. Resilient expansion of the foam upon removal of a compressive force can allow the pad 1032 to soak up or absorb at least some of the antiseptic 1033 that had previously been forced from the pad 1032. In some embodiments, the antiseptic 1033 can comprise any liquid antiseptic, such as alcohol, Isopropyl alcohol at various concentrations ranging from 50-90%, ethanol at various concentrations ranging from 50-95%, and combinations of any alcohols with any antiseptics, or a dry material, such as chlorhexidine gluconate, ethylenediaminetetraacetic acid (EDTA), Iodaphors, or any combination thereof. Accordingly, although the antiseptic 1033 is schematically depicted in FIG. 10 as a series of droplets, the antiseptic 1033 is not necessarily liquid and may fill the pad 1032 to a greater or lesser extent. In the illustrated embodiment, when the sterilization chamber 1022 is in a sealed state (e.g., in its pre-use condition), the pad 1032 is in a relaxed, expanded, or uncompressed state in a longitudinal direction. It is noted that the pad 1032 may be uncompressed in one or more dimensions, yet compressed in one or more other dimensions, when the assembly 1000 is in the pre-use state. For example, the pad 1032 can be expanded or in a relaxed state in a longitudinal direction, yet compressed radially inwardly via the sidewall 1012, when the assembly 1000 is in the pre-use state. Such a lack of compression of the pad 1032 in the longitudinal direction can result from the fact that the cap 1004 does not interact with the connection interface 1030 of the cap 1002 to seal the cap 1002, and thus no portion of the cap 1004 contacts the pad 1032 when the caps 1002, 1004 are in the pre-use configuration.

In the illustrated embodiment, the pad 1032 is substantially cylindrical and defines an outer diameter that is approximately the same size as an inner diameter of the threads 1031. In other embodiments, the outer diameter of the pad 1032 can be larger than the inner diameter of the threads 1031 so as to be radially compressed and held tighter within the sterilization chamber 1022. In further embodiments, the pad 1032 can include threading that projects radially inwardly and that is complementary to the threads 1031 to thereby secure the pad 1032 within the chamber 1022.

The sterilization chamber 1022 can be sealed at the sealing surface 1016 via a cover 1034 that can span an open end of the sterilization chamber 1022. The cover 1034 can be secured to the housing 1010 in any suitable manner, such as, for example, via an adhesive. Preferably, the cover 1034 can be readily removed by a practitioner. For example, in some embodiments, the cover 1034 can include a tab 1035 and a practitioner can readily remove the cover 1034 by holding the housing 1010 in one hand and pulling the tab 1035 away from the housing 1010 with the other hand. The removable cover 1034 can be formed of any suitable material, such as, for example, an impervious pliable material (e.g., foil, plastic, metallized-surface mylar, and the like). The cover 1034 can provide a hermetic seal that can assist in maintaining the sterility of the sterilization chamber 1022 prior to use of the cap 1002 and/or can prevent evaporative loss of antiseptic 1033 from the sterilization chamber 1022.

When the cap 1002 is coupled with a medical connector, the coupling action can bring a portion of the medical connector into contact with the pad 1032 and can allow the pad 1032 to wipe or scrub the medical connector, as described above. Likewise, the antiseptic 1033 can be forced into contact with the medical connector during the coupling phase and can remain in contact with the medical connector, while the cap 1002 is coupled with the medical connector. The connection interface 1030 can cooperate with a connection interface of the medical connector to maintain the cap 1002 in an attached configuration relative to the connector. Moreover, the connection interface 1030 can couple with the medical connector, such as via complementary threading, so as to prevent antiseptic from leaking from the sterilization chamber 1022.

In some embodiments, such as where the pad 1032 is formed of a material that is not fully elastically resilient or that requires a relatively long relaxation time in which to transition from a compressed state to a relaxed or uncompressed state (e.g., in a longitudinal direction), pre-use storage in the relaxed or uncompressed state in at least one dimension can preserve or enhance the cleaning, scrubbing, or sterilization properties of the pad 1032. For example, as the cap 1002 is coupled with the medical connector (e.g., the medical connector 132 of FIG. 4), an end of the medical connector can come into contact with a proximal surface (e.g., the surface furthest from the partition 1020) of the pad 1032. Further advancement of the cap 1002 onto the medical connector can cause the pad 1032 to deform to complement a contour of the end of the medical connector as the pad 1032 is compressed, which can permit a relatively tight or continuous contact between the pad 1032 and the medical connector. In the illustrated embodiment, the cap 1002 is rotated relative to the medical connector, as it is advanced onto the medical connector. This rotational motion causes the contoured surface of the pad 1032 to rub the medical connector. In certain embodiments, increasingly greater compression of the pad 1032 yields increasingly stronger rubbing of the medical connector, coupled with greater amounts of the antiseptic 1033 being expelled from the pad 1032. Accordingly, when the pad 1032 is uncompressed in at least one dimension (e.g., in a longitudinal direction) in a pre-use state, and thus is not plastically deformed or is not subject to time-consuming elastic recovery from pre-compression, the pad 1032 can be in sanitizing contact with the medical connector for a relatively greater portion of the coupling procedure. In some embodiments, a practitioner can more quickly couple the cap 1002 to the medical connector, as there is no need to first wait for the pad 1032 to relax to an uncompressed or expanded state to achieve better sterilization of the medical connector.

Various parameters can be adjusted to determine the amount of antiseptic 1033 that is expelled from the pad 1032 when the cap 1002 is coupled with a medical connector. For example, the depth to which the medical connector is received within the sterilization chamber 1022, the concentration of antiseptic 1033 within the pad 1032, and/or other parameters can be altered. In various embodiments, no less than about ¼, no less than about ⅓, no less than about ½, no less than about ⅔, or no less than about ¾ of the antiseptic 1033 is expelled from the pad 1032 when the cap 1002 is coupled with a medical connector. In some embodiments, all, or substantially all, of the antiseptic 1033 is expelled from the pad 1032.

With reference to FIG. 10, an interior surface the sidewall 1012 can include another connection interface 1040 in the region of the coupling chamber 1024. The connection interface 1040 can be configured to complementarily engage a connection interface 1042 of the cap 1004. For example, in the illustrated embodiment, the connection interface 1040 of the cap 1002 comprises inwardly projecting threads 1041, and the connection interface 1042 of the connector 1004 comprises outwardly projecting threads 1043 complementary thereto at an exterior surface of the cap 1004. The connection interfaces 1040, 1042 thus can allow the caps 1002, 1004 to be coupled to each other in a secure, yet selectively removable fashion. Other configurations of the connection interfaces 1040, 1042 may similarly permit the caps 1002, 1004 to be coupled with each other in a secure, yet selectively removable fashion, such as friction-fit, snap-fit, or other suitable interfacing arrangements. The coupling chamber 1024 can further include a sealing member 1044, such as an elastomeric gasket described further below.

With reference to FIGS. 10 and 11, the cap 1004 can comprise a housing 1050. The housing 1050 can be elongated, and may define a stepped, substantially cylindrical shape, or may define any other suitable shape. For example, in the illustrated embodiment, the housing 1050 includes a sidewall 1052, which is substantially cylindrical, and a base wall 1054 at one end of the sidewall 1052. A sealing end 1056 of the sidewall 1052 can be located opposite the base wall 1054, and can define an opening into a sterilization chamber 1058. The sidewall 1052 and the base wall 1054 thus can cooperate to define the sterilization chamber 1058.

In some embodiments, the housing 1050 includes a skirt 1060, which can extend radially outwardly from the sidewall 1052. In some embodiments, the skirt 1060 provides a convenient surface for manipulation of the cap 1004. For example, in some embodiments, an outer diameter of the sidewall 1052 is smaller than an outer diameter of the sidewall 1012 of the cap 1002 such that the disparity between the outer diameters could complicate the gripping and rotation of the caps 1002, 1004 relative to each other. Moreover, in some embodiments, the sidewall 1052 defines a relatively small outer surface area, which could make it difficult to grip the cap 1004. The larger outer diameter and corresponding larger surface area of the skirt can facilitate gripping of the cap 1004. The outer surface of the skirt 1060 can be smooth, as shown, or may include gripping features, which can aid in rotating the cap 1004 relative to the cap 1002 to permit separation of the caps 1002, 1004 and/or aid in rotating the cap 1004 relative to a medical connector. Such gripping features can include, for example, ridges, grooves, and/or protrusions similar to the ridges 105, grooves 107, and protrusions 108 described above and/or an elastomeric or other coating having a relatively high coefficient of friction.

In some embodiments, a terminal edge 1062 of the skirt 1060 can be substantially coplanar with an outer surface of the base wall 1054. In certain of such embodiments, the skirt 1060 can increase the stability of the assembly 1000. For example, the assembly 1000 can stand uprightly on the base wall 1054, and the skirt 1060 can inhibit tipping of the assembly 1000.

With reference to FIG. 10, the sterilization chamber 1058 can include a pad 1070 such as the pad 1032. The pad 1070 can be deformable, so as to conform to the contours of a portion of a medical connector that is introduced into the sterilization chamber 1058 (e.g., an outer surface of a male luer). Compression and/or decompression of the pad 1070 can cause an antiseptic 1033 to exit from and/or be absorbed by the pad 1070, respectively, in a manner such as described above with respect to the pad 1032 (it is noted that the antiseptic 1033 used with the pad 1070 need not necessarily be the same antiseptic as that used with the pad 1032, although such is possible). Likewise, scrubbing or sanitization of a medical connector via the pad 1070 can proceed in a manner such as that described above with respect to the pad 1032. In the illustrated embodiment, the pad 1070 is in a relaxed or uncompressed state in at least a longitudinal direction when the sterilization chamber 1058 is in a sealed or pre-use configuration.

As previously discussed, the cap 1004 can include the connection interface 1042, which can interact with the connection interface 1040 of the cap 1002. The connection interfaces 1040, 1042 can cooperate to hold the cap 1004 tightly against the sealing member 1044. For example, where the connection interfaces 1040, 1042 comprise threading, appropriate rotation of the cap 1004 relative to the cap 1002 can draw the sealing end 1056 of the sidewall 1052 into abutment with the sealing member 1044, and additional rotation in the same direction may deform the sealing member 1044. The sealing end 1056 and the sealing member 1044 can form a hermetic seal that can assist in maintaining the sterility of the sterilization chamber 1058 prior to use of the cap 1004, and can prevent evaporative loss of an antiseptic from the sterilization chamber 1058. In further embodiments, a sealing tape (not shown), such as the sealing tape 158 (see FIGS. 8A and 8B), can be positioned about the caps 1002, 1004 so as to contact a lower edge of the housing 1010 (e.g., an outer surface of the portion of the sidewall 1012 that defines the coupling chamber 1058) and an outer surface of the skirt 1060 of the housing 1050. The tape can aid in preventing evaporative loss of the antiseptic and/or can indicate whether the caps 1002, 1004 have been separated or otherwise moved from their initial or pre-use configuration. For example, in some embodiments, the tape can be frangible.

In the illustrated embodiment, the connection interface 1042 comprises outwardly projecting threads similar to the threads 114 described above, and can be configured to complementarily engage a connection interface of a medical connector, such as, for example, inwardly projecting threads of a skirt that surrounds a male luer. The threaded connection interface 1042 thus can allow for selective coupling of the cap 1004 to a medical connector in a secure, yet selectively removable fashion. Other configurations of the connection interface 1042 may permit the cap 1004 to be coupled with a medical connector in a secure, yet selectively removable fashion, such as friction-fit, snap-fit, or other suitable interfacing arrangements.

With continued reference to FIG. 10, additional description of the illustrated embodiment of the assembly 1000 in the pre-use state will now be provided. As previously discussed, each sterilization chamber 1022, 1058 can be defined by a separate housing 1012, 1050. The chambers 1022, 1058 can be isolated from each other in the pre-use condition, or stated otherwise, no fluid communication may exist between the chambers 1022, 1058.

The caps 1002, 1004 can cooperate to seal one of the chambers (e.g., the chamber 1058 in the illustrated embodiment) such that manipulation of the caps 1002, 1004 away from their pre-use configuration can unseal the chamber 1058, whereas the other chamber (e.g., the chamber 1022 in the illustrated embodiment) can remain in a sealed orientation independent of the relative orientations of the caps 1002, 1004. At least a portion of the housing 1050 of the cap 1004 can be received within, or can nest within, a portion of the housing 1010 of the cap 1002. In the illustrated embodiment, the pads 1032 is free of any compression from the cap 1004 and the pad 1070 is free of any compression from the cap 1002 when the sterilization chambers 1022, 1058 in which is the pads 1032, 1070 are housed are in a pre-use, sealed condition.

In the illustrated embodiment, the caps 1002, 1004 are substantially coaxial with each other. As previously discussed, the sterilization chambers 1022, 1058 defined by the caps 1002, 1004 each can have an open end and a closed end, and in the pre-use configuration, the chambers 1022, 1058 can be oriented such that their sealed open ends face in the same direction along the common axis of the caps 1002, 1004.

With reference to FIG. 11, in order to prepare the cap 1004 for use with a medical connector (e.g., the connector 136 of FIG. 5), the caps 1002, 1004 are decoupled from each other. For example, in the illustrated embodiment, the caps 1002, 1004 are rotated in opposite directions about a common longitudinal axis such that the connection interfaces 1040, 1042 urge the caps 1002, 1004 away from each other and are eventually released from each other. The cap 1004 can then be coupled with the medical connector via the connection interface 1042, such as in a secure, yet selectively removable manner.

The cap 1002 can be prepared for use with a medical connector (e.g., the connector 132 of FIG. 4) and connected to the medical connector independent of the coupling status of the caps 1002, 1004 relative to each other. The cover 1034 can be removed from the cap 1002, thereby permitting the cap 1002 to be coupled with the medical connector via the connection interface 1040, such as in a secure, yet selectively removable manner.

The pre-use configuration of the system 1000, in which the caps 1002, 1004 are coupled with each other, can ease clinician handling of the system 1000. As the caps 1002, 1004 may be used to cover female and male connectors, respectively, immediately upon decoupling of the female and male connectors from each other, having the caps 1002, 1004 available in a coupled yet easily separable configuration can be convenient and time saving. Moreover, the system 1000 can include relatively few parts, which can reduce manufacturing costs. In some embodiments, the pre-use coupled configuration of the caps 1002, 1004 likewise can reduce packaging costs of the system 1000.

FIG. 12 illustrates another embodiment of an assembly 1100, which can resemble the assembly 1000 described above in certain respects. Accordingly, like features are designated with like reference numerals, with the leading digits incremented to "11." Relevant disclosure set forth above regarding similarly identified features thus may not be repeated hereafter. Moreover, specific features of the assembly 1100 may not be identified by a reference numeral in the drawings or specifically discussed in the written description that follows. However, such features may clearly be the same, or substantially the same, as features depicted in other embodiments and described with respect to such embodiments. Accordingly, the relevant descriptions of such features apply equally to the features of the assembly 1100. Any suitable combination of the features and variations of the same described with respect to the assembly 1000 and components thereof can be employed with the assembly 1100 and components thereof, and vice versa. This pattern of disclosure applies equally to further embodiments depicted in subsequent figures and described hereafter.

As with the assembly 1000, the assembly 1100 can include a cap 1102 and a cap 1104 that are coupled with each other when in a pre-use state and that can be removed from each other. The cap 1102 can be configured to couple with a female connector, and the cap 1104 can be configured to couple with a male connector. The cap 1102 can include a housing 1110, which can include a sidewall 1112 and a partition 1120. A portion of the sidewall 1112 can cooperate with the partition 1120 to define a sterilization chamber 1122 such as the sterilization chamber 1022. In the illustrated embodiment, the sterilization chamber 1122 is somewhat shorter than the sterilization chamber 1022 (see FIG. 10). The sterilization chamber 1122 can include a connection interface 1130, which, in the illustrated embodiment, includes threading 1131. The sterilization chamber 1122 can include a pad 1132, such as the pad 1032, and can be sealed via a removable cover 1134.

Another portion of the sidewall 1112 can cooperate with the partition 1120 to define a coupling chamber 1124 that extends in a direction opposite the sterilization chamber 1122. A terminal edge 1118 of the sidewall 1112 can define an opening of the sterilization chamber 1122. The sidewall 1112 can define a connection interface 1140 that is configured to aid in coupling the caps 1102, 1104 with each other, as described further below.

With continued reference to FIG. 12, the cap 1104 can include a housing 1150 that includes a sidewall 1152 and a base wall 1154. The sidewall 1152 and the base wall 1154 can cooperate to define a sterilization chamber 1158, which can include a pad 1170 therein. The sterilization chamber 1158 can be sealed at a sealing end 1156 of the sidewall 1152 via a removable cover 1136, which can resemble the cover 1134. A portion of the sidewall 1152 can define a connection interface 1142, which includes one or more threads 1143 in the illustrated embodiment.

The housing 1150 can define a skirt 1160 that projects radially outwardly from the sidewall 1152. The skirt 1160 can terminate at a terminal edge 1162. In the illustrated embodiment, the skirt 1160 is shorter than the skirt 1060 of the housing 1050 (see FIG. 10) and is spaced above a plane that is defined by an outer surface of the base wall 1154. In some embodiments, the terminal edge 1162 contacts or is in close proximity to the terminal edge 1118 of the housing 1110 when the caps 1102, 1104 are coupled with each other in a pre-use configuration, which can provide continuity to an outer surface of the assembly 1100 when it is in a pre-use configuration. The skirt 1160 can be rounded or beveled at the terminal edge 1162, and an end of the sidewall 1112 can be rounded or beveled at the terminal edge 1118, which can provide the system 1100 with an annular recess 1163 that can provide a visual and/or tactile indication of the transition from the skirt 1160 to the sidewall 1112. The rounded ends can also enhance practitioner and/or patient comfort during use of the caps 1102, 1104.

In the illustrated embodiment, the sidewall 1152 of the housing 1150 defines a connection interface 1180 that is configured to couple with the connection interface 1140 of the housing 1110. In particular, the connection interface 1180 includes an outward projection 1181 and the connection interface 1140 includes a recess 1144 that extends radially outwardly relative to the connection chamber 1124 and that is sized to receive the annular projection 1181 therein in a snap-fit engagement. In the illustrated embodiment, each of the projection 1181 and the recess 1144 is annular and extends about the cap 1104 and the cap 1102, respectively, in its entirety. In other embodiments, the projection 1181 and/or the recess 1144 extend about only a portion of the caps 1102, 1104. In still other or further embodiments, the connection interface 1180 can include a recess in the sidewall 1152 and the connection interface 1140 can include an inward projection sized to fit within the recess in a snap-fit engagement. In still other or further embodiments, the connection interfaces 1140, 1180 can include complementary threading, such as the connection interfaces 1040, 1042 described above. Other coupling arrangements are also possible.

Features, usage, and operation of the assembly 1100 can resemble that of the assembly 1000 described above. For example, when the assembly 1100 is in the pre-use condition, each sterilization chamber 1122, 1158 can be defined by a separate housing 1112, 1150, and the sterilization chambers 1122, 1158 can be fluidly isolated from one another (e.g., no fluid communication may exist between the sterilization chambers 1122, 1158). Likewise, at least a portion of the housing 1150 of the cap 1104 can be received within, or can nest within, a portion of the housing 1110 of the cap 1102. In the illustrated embodiment, each of the pads 1132, 1170 is in an uncompressed or expanded state when the sterilization chamber 1122, 1158 in which it is housed is in a pre-use, sealed condition.

However, certain differences can exist between the assembly 1100 and the assembly 1000. For example, each of the sterilization chambers 1122, 1158 can remain sealed independent of the coupling status of the caps 1102, 1104. Stated otherwise, the caps 1102, 1104 do not cooperate to seal either of the chambers 1122, 1158. Accordingly, one or both of the caps 1102, 1104 can be unsealed (e.g., the covers 1134, 1136 can be removed) and coupled with a separate medical connector (e.g., via the connection interfaces 1130, 1142) without detaching the caps 1102, 1104 from each other. Stated in yet another manner, either of the caps 1102, 1104 can be installed on a medical connector without being detached from and/or without unsealing the other cap 1102, 1104. Alternatively, the caps 1102, 1104 can be detached from each other, one or both of the caps 1102, 1104 each can be connected with a separate medical connector (i.e., via the connection interfaces 1130, 1142), and the caps 1102, 1104 can be reattached to each other (i.e., via the connection interfaces 1140, 1180), while remaining connected to the one or more medical connectors.

Moreover, in the illustrated embodiment, the caps 1102, 1104 are substantially coaxial with each other, thus resembling the caps 1002, 1004. However, the sterilization chambers 1122, 1158 are oriented such that their sealed open ends face away from each other (e.g., outwardly in opposite directions) along the common axis of the caps 1102, 1104, when the assembly 1100 is in the pre-use configuration.

FIG. 13 illustrates another embodiment of an assembly 1200, which can resemble one or more of the assemblies described above in certain respects. Accordingly, like features are designated with like reference numerals, with the leading digits incremented to "12." As with the assembly 1100, the assembly 1200 can include a cap 1202 and cap 1204 that are coupled with each other, when in a pre-use state, and that can be removed from each other.

The caps 1202, 1204 can differ from the caps 1102, 1104 in the manner by which they are coupled with each other. In particular, the cap 1202 includes a housing 1210 that defines a connection chamber 1224 configured to receive a portion of a housing 1250 of the cap 1204. The housing 1210 defines a connection interface 1240, and the housing 1250 defines a connection interface 1280. Rather than cooperating in a snap-fit engagement, however, the connection interfaces 1240, 1280 cooperate with each other in a friction-fit engagement to provide a secure attachment between the caps 1202, 1204 and yet to permit the caps 1202, 1204 to be selectively removable from each other and to permit selective reattachment of the caps 1202, 1204 to each other. Features, usage, and operation of the assembly 1200 can otherwise resemble that of the assembly 1100 described above.

Figure 15:
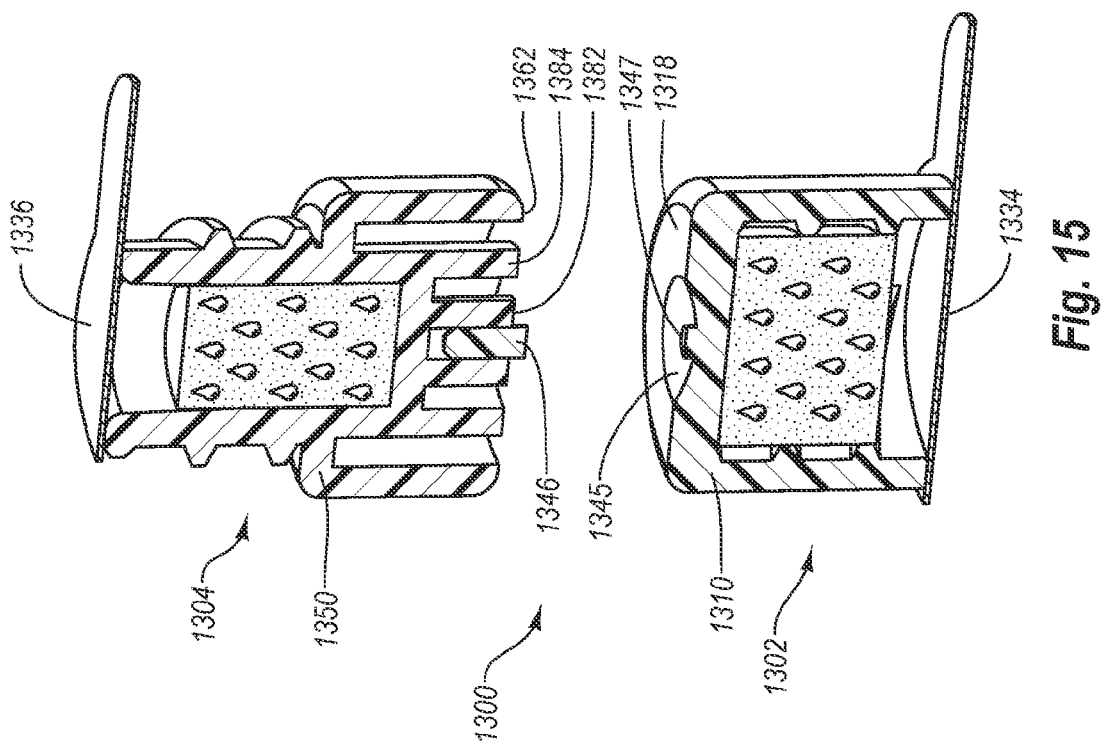
FIG. 15 is a cross-sectional perspective view of the assembly of FIG. 14 showing the caps detached from each other.
Figure 14:
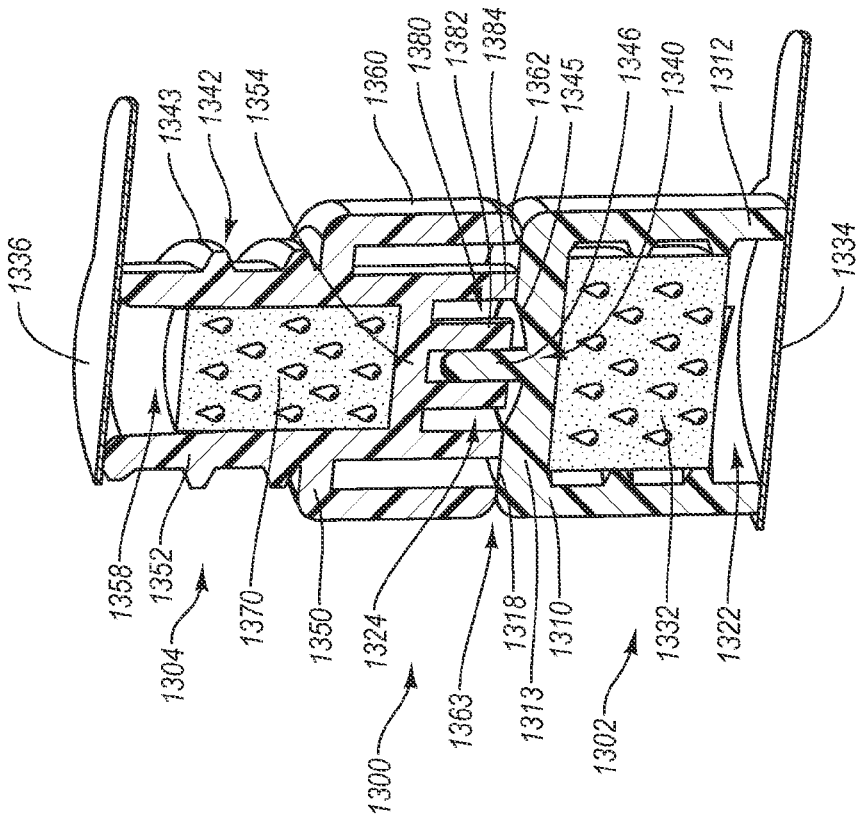
FIG. 14 is a cross-sectional perspective view of another embodiment of an assembly that includes a pair of caps, which are attached to each other via a press-fit interface.

FIGS. 14 and 15 illustrate another embodiment of an assembly 1300, which can resemble one or more of the assemblies described above in certain respects. Accordingly, like features are designated with like reference numerals, with the leading digits incremented to "13." The assembly 1300 can include a cap 1302 and cap 1304 that are coupled with each other when in a pre-use state and that can be removed from each other. However, as discussed further below, the caps 1302, 1304 can include connection interfaces 1340, 1380, respectively, that attach the caps 1302, 1304 to each other in a pre-use configuration, and that permit ready detachment of the caps 1302, 1304 one from another, but that do not themselves permit reattachment of the caps 1302, 1304.

The cap 1302 can include a housing 1310, which can include a sidewall 1312 and a base wall 1313. The sidewall 1312 and the base wall 1313 can cooperate to define a sterilization chamber 1322 that can include a pad 1332 therein and that can be sealed via a removable cover 1334. The base wall 1313 can include a terminal surface 1318 and can define the connection interface 1340. In the illustrated embodiment, the connection interface 1340 includes a depression or recess 1345 that bows the terminal surface 1318 inwardly, or toward the sterilization chamber 1322. The connection interface 1340 further includes a pin 1346 that extends outwardly, or away from the sterilization chamber 1322.

With continued reference to FIGS. 14 and 15, the cap 1304 can include a housing 1350 that includes a sidewall 1352 and a base wall 1354. The sidewall 1352 and the base wall 1354 can cooperate to define a sterilization chamber 1358, which can include a pad 1370 therein. The sterilization chamber 1358 can be sealed via a removable cover 1336. A portion of the sidewall 1352 can define a connection interface 1342, which includes one or more threads 1343 in the illustrated embodiment.

The housing 1350 can define a skirt 1360 that projects radially outwardly from the sidewall 1352. The skirt 1360 can terminate at a terminal edge 1362. In the illustrated embodiment, the skirt 1360 extends past a plane that is defined by an outer surface of the base wall 1354 and is sufficiently long to permit the terminal edge 1362 thereof to contact the terminal surface 1318 of the housing 1310 when the caps 1302, 1304 are in a pre-use configuration. As with the skirt 1160 and the sidewall 1112, the skirt 1360 can be rounded or beveled at its terminal edge 1362, and the sidewall 1112 can be rounded or beveled at the terminal surface 1118, which can provide the system 1300 with an annular recess 1363.

The housing 1350 defines the connection interface 1380, which is configured to couple with the connection interface 1340 of the housing 1310. The connection interface 1380 includes a protrusion 1382 that extends from the base wall 1354 in a direction opposite the sterilization chamber 1358. The protrusion 1382 is sized and shaped to receive therein at least a portion of the pin 1346, and may be substantially annular. In various embodiments, the protrusion 1382 is joined to the pin in any suitable manner, such as, for example, press-fit or friction-fit engagement and/or any suitable adhesive.

In the illustrated embodiment, an additional protrusion 1384 is coaxial with and encircles the protrusion 1382, and may also be substantially annular. The protrusion 1384 can contact the terminal surface 1318 of the housing 1310 when the caps 1302, 1304 are in a pre-use configuration, and can provide stability to the connection interfaces 1340, 1380 and assist in preventing premature separation of the caps 1302, 1304. The protrusion 1384 can be said to define a connection chamber 1324 in which the connection interface 1380 is located.

As shown in FIG. 15, the caps 1302, 1304 can be separated from each other, which can facilitate coupling of the caps 1302, 1304 to separate medical connectors by removing a constraint on the range of motion of the caps 1302, 1304 relative to each other. In the illustrated embodiment, the pin 1346 can be sufficiently thin, sufficiently weak, or otherwise configured to break away from the housing 1310, and can remain attached to the protrusion 1382 of the housing 1350. In various embodiments, in order to break the pin 1346, a practitioner can rotate the caps 1302, 1304 relative to each other about their common longitudinal axis and/or can rotate one or more of the caps 1302, 1304 about an axis perpendicular to its longitudinal axis so as to move the longitudinal axes of the caps 1302, 1304 out of alignment with each other.

Breaking the pin 1346 can leave a nub 1347 on the housing 1310. In certain embodiments, the nub 1347 can be fully below the terminal surface 1318 of the housing 1310 due to the recess 1345, which can prevent or reduce contact with the nub 1347, such as by a patient or practitioner.

In certain embodiments, the connection interfaces 1340, 1380 are configured so as to not rejoin with each other once the caps 1302, 1304 have been separated from the pre-use configuration. For example, once the pin 1346 has been broken, the caps 1302, 1304 cannot readily be rejoined to each other via the pin 1346. Accordingly, the caps 1302, 1304 can be configured to be attached with each other in a pre-use configuration and readily separated from each other as desired, but not readily rejoined with each other once separated.

Features, usage, and operation of the assembly 1300 can resemble those of one or more of the assemblies described above in other respects. For example, when the assembly 1300 is in the pre-use condition, each sterilization chamber 1322, 1358 can be defined by a separate housing 1312, 1350, and the sterilization chambers 1322, 1358 can be fluidly isolated from one another. Likewise, at least a portion of one of the housings 1310, 1350 can be received within, or can nest within, a portion of the other housing 1310, 1350. To this end, it is noted that in other embodiments of the assembly 1300, the housing 1350 of the cap 1304 may define the pin 1346 (or, more generally, the connection interface 1340), and the housing 1310 of the cap 1302 may define the annular extension 1382 (or, more generally, the connection interface 1380). In the illustrated embodiment, each of the pads 1332, 1370 is in an uncompressed or expanded state when the sterilization chamber 1322, 1358 in which it is housed is in a pre-use, sealed condition. Like the assemblies 1100, 1200, each of the sterilization chambers 1322, 1358 can remain sealed independent of the coupling status of the caps 1302, 1304. One or both of the sterilization chambers 1322, 1358 can be opened and used, while the caps 1302, 1304 are connected with each other, or the caps 1302, 1304 can be separated from each other and one or both of the sterilization chambers 1322, 1358 can then be opened and each used with a separate medical connector.

Figure 17:
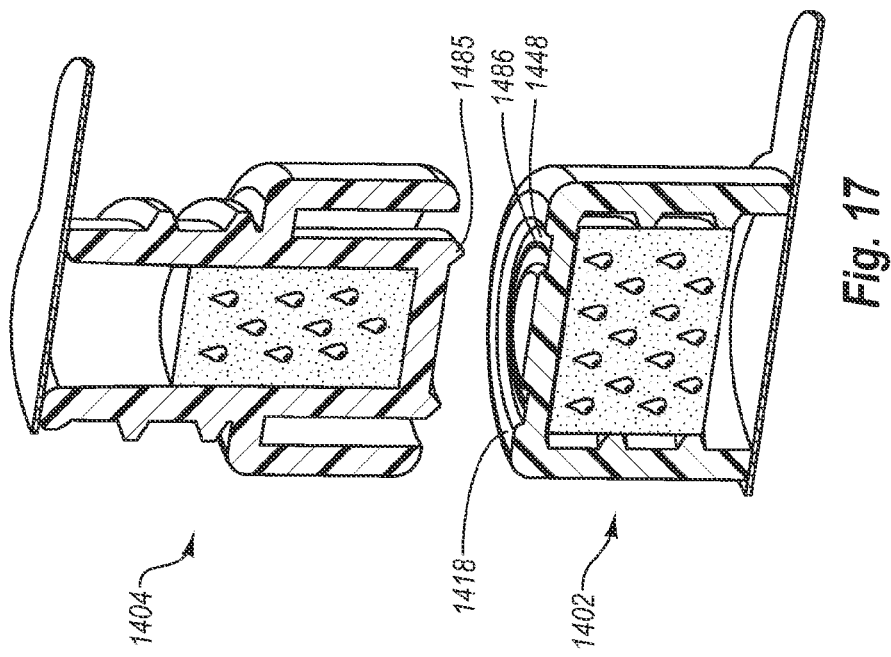
FIG. 17 is a cross-sectional perspective view of the assembly of FIG. 16 showing the caps detached from each other.
Figure 16:
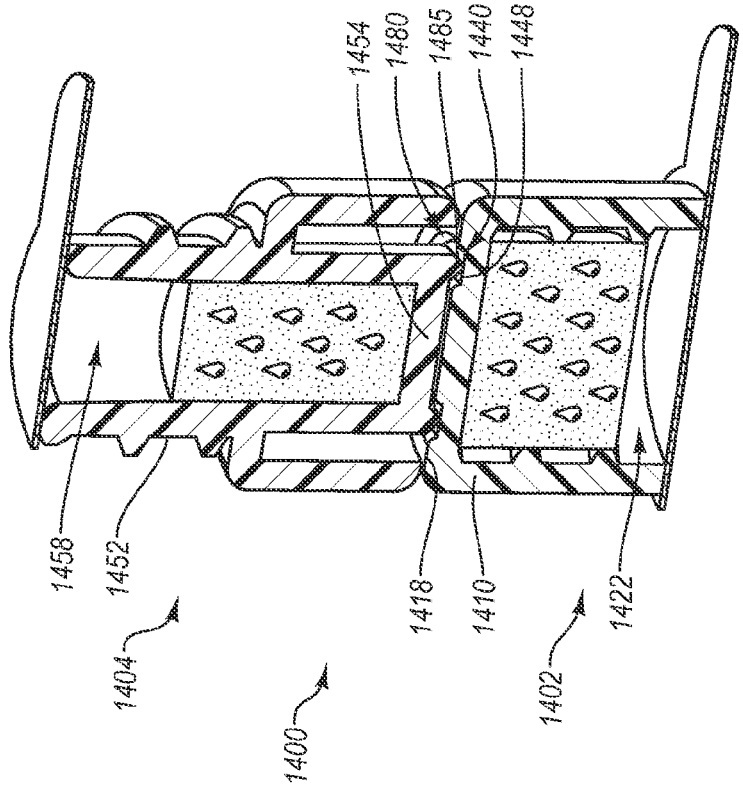
FIG. 16 is a cross-sectional perspective view of another embodiment of an assembly that includes a pair of caps, which are attached to each other via a welded interface.

FIGS. 16 and 17 illustrate another embodiment of an assembly 1400, which can resemble the assembly 1300 described above in certain respects. Accordingly, like features are designated with like reference numerals, with the leading digits incremented to "14." The assembly 1400 can include a cap 1402 and cap 1404 that are coupled with each other when in a pre-use state, and that can be removed from each other in a manner similar to the caps 1302, 1304. However, connection interfaces 1440, 1480 of the caps differ from the connection interfaces 1340, 1380 of the caps 1302, 1304.

The connection interface 1440 can be defined by a terminal surface 1418 of a housing 1410 of the cap 1402. The connection interface 1440 can include a depression or recess 1448 that bows the terminal surface 1418 inwardly, or toward a sterilization chamber 1422. The recess 1448 can be annular, although other shapes and configurations are possible.

A sidewall 1452 of the cap 1404 can be somewhat longer than the sidewall 1352 of the cap 1304, and a base wall 1454 of the cap 1404 can be in close proximity with or adjacent to the terminal surface 1418 of the cap 1402. A protrusion 1485 can extend outwardly from the base wall 1454, or in a direction away from a sterilization chamber 1458. The protrusion 1485 can be annular so as to be received within the annular recess 1448, although other shapes and configurations are possible. The protrusion 1485 can be joined to the recess 1448 in any suitable manner, such as via an adhesive or via welding (e.g., spin, ultra-sonic, laser, radio frequency, thermal, etc.).

In the illustrated embodiment, the protrusion 1485 is welded to the recess 1448, and the weld is configured to be broken to permit separation of the caps 1402, 1404. As shown in FIG. 17, a weld edge 1486 can remain within the recess 1448 when the caps 1402, 1404 are separated. In certain embodiments, the weld edge 1486 can be fully below the terminal surface 1418 of the housing 1410, which can prevent or reduce contact with the weld edge 1486, such as by a patient or practitioner. In order to break the weld, a practitioner can rotate the caps 1402, 1404 relative to each other about their common longitudinal axis and/or can rotate one or more of the caps 1402, 1404 about an axis perpendicular to its longitudinal axis, so as to move the longitudinal axes of the caps 1402, 1404 out of alignment with each other. In other embodiments, the connection interfaces 1440, 1480 can be reversed such that the cap 1402 includes the protrusion 1485 and the cap 1404 can includes the recess 1448.

Figure 18:
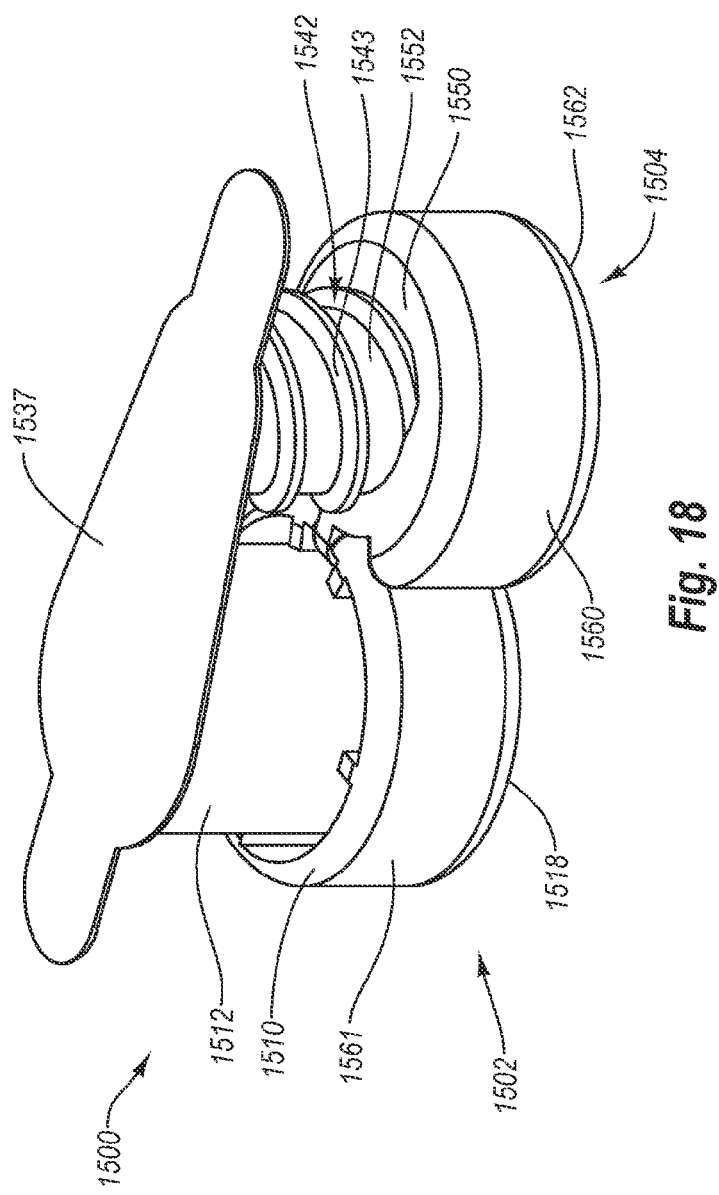
FIG. 18 is a perspective view of another embodiment of an assembly that includes a pair of caps, which are attached to each other at least partially via a snapping interface.
Figure 19:
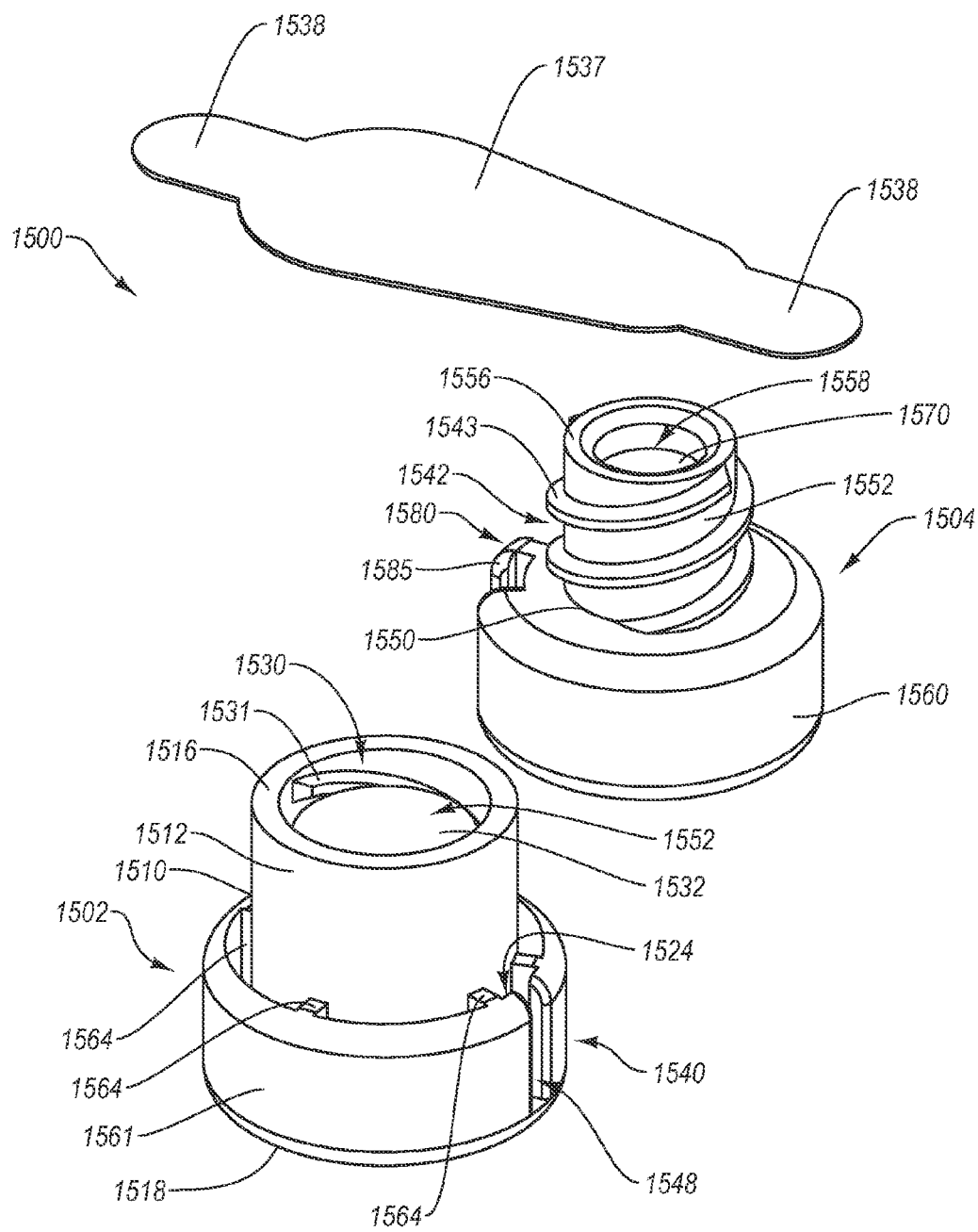
FIG. 19 is a perspective view of the assembly of FIG. 18 showing the caps detached from each other.

FIGS. 18-21 illustrate another embodiment of an assembly 1500, which can resemble one or more of the assemblies described above in certain respects. Accordingly, like features are designated with like reference numerals, with the leading digits incremented to "15." As can be seen in FIGS. 18 and 19, and as discussed hereafter, the assembly 1500 can include a cap 1502 and cap 1504 that are coupled with each other when in a pre-use state and that can be removed from each other. The cap 1502 can be configured to couple with a female connector, and the cap 1504 can be configured to couple with a male connector. The caps 1502, 1504 can be in a side-by-side arrangement when connected to each other in a pre-use configuration. In the illustrated embodiment, both caps 1502, 1504 can be sealed shut in the pre-use configuration via a common cover 1537.

The cap 1502 can include a housing 1510, which can include a sidewall 1512 and a base wall 1513. The sidewall 1512 can cooperate with the base wall 1513 to define a sterilization chamber 1522. The sterilization chamber 1522 can include a connection interface 1530, which, in the illustrated embodiment, includes threading 1531 disposed on an interior surface of the housing 1512. The connection interface 1530 can be configured to attach the cap 1502 to a medical connector in a secure yet selectively removable manner. The sterilization chamber 1522 can include a pad 1532.

Figure 21:
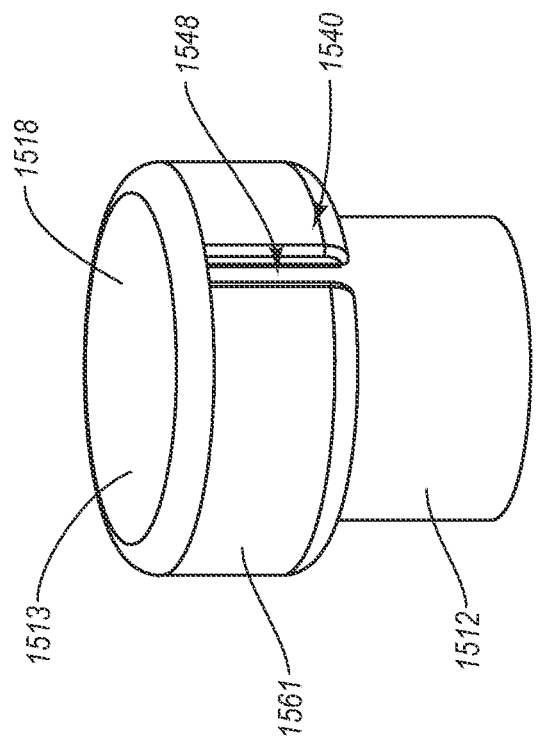
FIG. 21 is a perspective view from a different angle of another of the caps of FIG. 18.

The housing 1510 can further include a skirt 1561 that projects radially outwardly from the sidewall 1512 and that can also extend substantially parallel to the sidewall 1512. The skirt 1561 can include one or more spacers or supports 1564 that can provide structural rigidity to the skirt 1561. As shown in FIGS. 19 and 21, the housing 1510 can define a connection interface 1540 that is configured to aid in coupling the caps 1502, 1504 with each other in a pre-use configuration, as discussed further below. The connection interface 1540 can include a slot 1548 defined by the skirt 1561, which can extend in a direction substantially parallel to a longitudinal axis of the sterilization chamber 1522. The sidewall 1512 and the skirt 1561 can cooperate to define an open connection chamber 1524, which is also discussed below. The slot 1548 can define a side opening of the connection chamber 1524.

Figure 20:
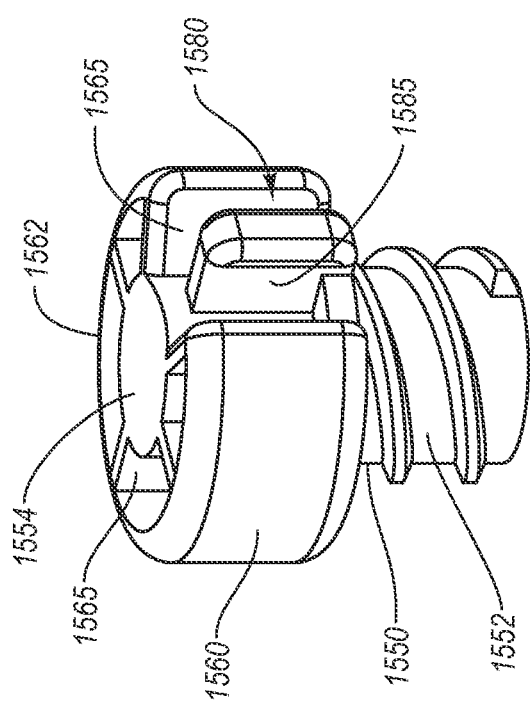
FIG. 20 is a perspective view from a different angle of one of the caps of FIG. 18.

With reference to FIGS. 19 and 20, the cap 1504 can include a housing 1550 that includes a sidewall 1552 and a base wall 1554. The sidewall 1552 and the base wall 1554 can cooperate to define a sterilization chamber 1558, which can include a pad 1570 therein. A portion of the sidewall 1552 can define a connection interface 1542, which includes one or more threads 1543 in the illustrated embodiment. The connection interface 1542 can be configured to attach the cap 1504 to a medical connector in a secure yet selectively removable manner. The housing 1550 can define a skirt 1560 that projects radially outwardly from the sidewall 1552 and that can also extend substantially parallel to the sidewall 1552. In the illustrated embodiment, the skirt 1560 extends about only a portion of the cap 1504. The skirt 1560 can include one or more spacers or supports 1565 that can provide structural rigidity to the skirt 1560.

The housing 1550 can further define a connection interface 1580 that is configured to interact with the connection interface 1540 of the housing 1510 to couple the caps 1502, 1504. The connection interfaces 1540 can maintain the caps 1502, 1504 in a pre-use configuration, and can permit the caps 1502, 1504 to be selectively removed from this configuration. In the illustrated embodiment, the connection interfaces 1540, 1580 can further interact with each other to permit selective reattachment of the caps 1502, 1504 to each other.

In the illustrated embodiment, the connection interface 1580 includes a locking member, snapping member, or radial extension 1585. The extension 1585 projects radially from the sidewall 1552 and includes an enlarged region at its outermost end. The extension 1585 is configured to be received within the slot 1548 and the connection chamber 1524 of the cap 1502. The enlarged portion of the extension 1585 can prevent the extension 1585 from moving out of the slot 1548 in a lateral direction. Although not shown, in some embodiments, the slot 1548 and the extension 1585 can include keying, such as a protrusion and recess that cooperate in a snapping fashion, which can selectively prevent the extension 1585 from moving out of the slot 1548 in a longitudinal direction in the absence of application of sufficient force by a practitioner. In other embodiments, the connection interfaces 1540, 1580 can be reversed such that the cap 1402 includes the extension 1585 and the cap 1504 includes the slot 1548.

In the illustrated embodiment, a terminal surface 1518 of the cap 1502 and a terminal surface 1562 of the cap 1504 are substantially coplanar when the system 1500 is in the pre-use configuration. This can contribute to the stability of the pre-use system 1500, as the connected system 1500 can be set on a planar surface without a predisposition to tipping. Likewise, in the illustrated embodiment, a sealing end 1516 of the cap 1502 and a sealing end 1556 of the cap 1504 are substantially coplanar when the system 1500 is in the pre-use configuration. Each sealing end 1516, 1556 can be sealed closed via a single or common removable cover 1537. In the illustrated embodiment, the cover 1537 includes two tabs 1538 that can permit selective opening of just one of the caps 1502, 1504, or the opening both of the caps 1502, 1504 by beginning with opening one of the caps 1502, 1504 by removing a portion of the cover 1537 from that cap 1502, 1504 and then continuing to remove the cover 1537 from the remaining cap 1502, 1504. Other arrangements are also possible.

The cover 1537 can assist in maintaining the caps 1502, 1504 coupled with each other in the pre-use configuration, as it can be sufficiently tight to resist longitudinal movement of the caps 1502, 1504 relative to each other. In various embodiments, the cover 1537 is removed from one or both of the caps 1502, 1504 prior to removing the caps 1502, 1504 from each other, as shown in FIG. 19. In other embodiments, the connection interfaces 1540, 1580 of the caps 1502, 1504 can be decoupled from each other prior to removing the cover 1537.

Features, usage, and operation of the assembly 1500 can resemble that of one or more of the assemblies described above. For example, when the assembly 1500 is in the pre-use condition, each sterilization chamber 1522, 1558 can be defined by a separate housing 1512, 1550, and the sterilization chambers 1522, 1558 can be fluidly isolated from one another. Likewise, at least a portion of the housing 1550 of the cap 1504 can be received within, or can nest within, a portion of the housing 1510 of the cap 1502. In the illustrated embodiment, each of the pads 1532, 1570 is in an uncompressed or expanded state when the sterilization chamber 1522, 1558 in which it is housed is in a pre-use, sealed condition.

However, certain differences can exist. For example, in the illustrated embodiment, the caps 1502, 1504 are side-by-side, rather than coaxial, when in the pre-use configuration. Stated otherwise, each cap 1502, 1504 can define a longitudinal axis, and the longitudinal axes can be substantially parallel with each other or non-collinear relative to each other when the caps 1502, 1504 are in the pre-use configuration. In the illustrated embodiment, the sterilization chambers 1522, 1558 are oriented such that their sealed open ends face in substantially the same direction when the assembly 1500 is in the pre-use configuration.

Figure 22:
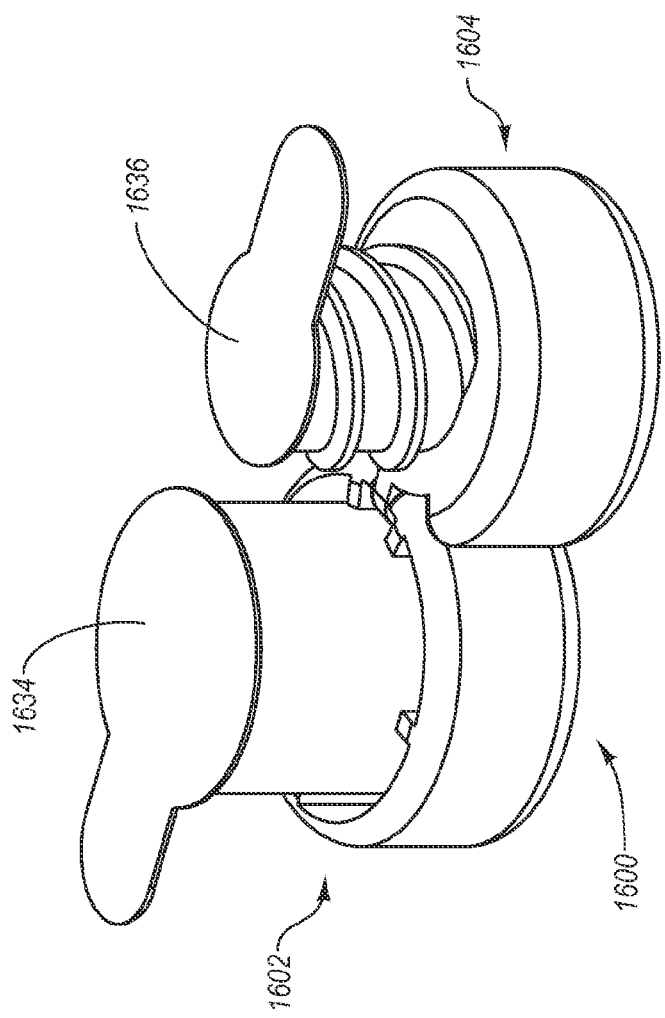
FIG. 22 is a perspective view of another embodiment of an assembly that includes a pair of caps, which are attached to each other via a snapping interface.

FIG. 22 illustrates another embodiment of an assembly 1600, which can resemble one or more of the assemblies described above, particularly the assembly 1500, in certain respects. Accordingly, like features are designated with like reference numerals, with the leading digits incremented to "16." The assembly 1600 can include caps 1602, 1604 such as the caps 1502, 1504. Rather than including a single cover 1537, however, an individual cover 1634, 1636 is provided to each of the caps 1602, 1604. Such an arrangement can, in some instances, facilitate removal of the caps 1602, 1604 from each other while the caps 1602, 1604 are maintained in a sealed configuration.

Figure 23:
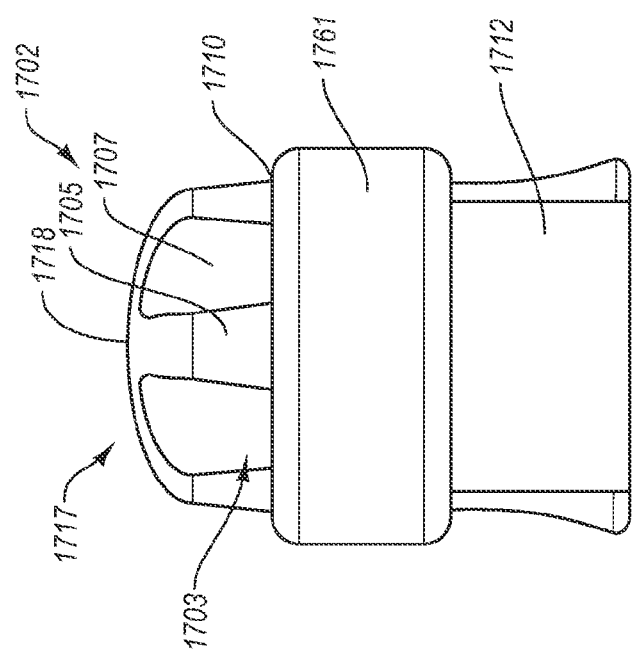
FIG. 23 is a side elevation view of an embodiment of a cap that is compatible with at least the assemblies of FIGS. 18 and 22.

FIG. 23 illustrates an embodiment of a cap 1702 that can be used in the place of the caps 1502, 1602 in the systems 1500, 1600. The cap 1702 can include a housing 1710 that includes a sidewall 1712 and a skirt 1761. The sidewall 1712 can taper radially outwardly with increasing distance from the skirt 1761. Moreover, the housing 1710 can include an extension region 1717 that projects in an opposite direction from the skirt 1761. The extension region 1717 can include a rounded terminal surface 1718. The cap 1702 thus can more closely resemble the cap 102 described above. For example, the extension region 1717 can include gripping features 1703, such as ridges 1705 and grooves 1707. Similar alterations can be made to the caps 1504, 1604.

Figure 24:
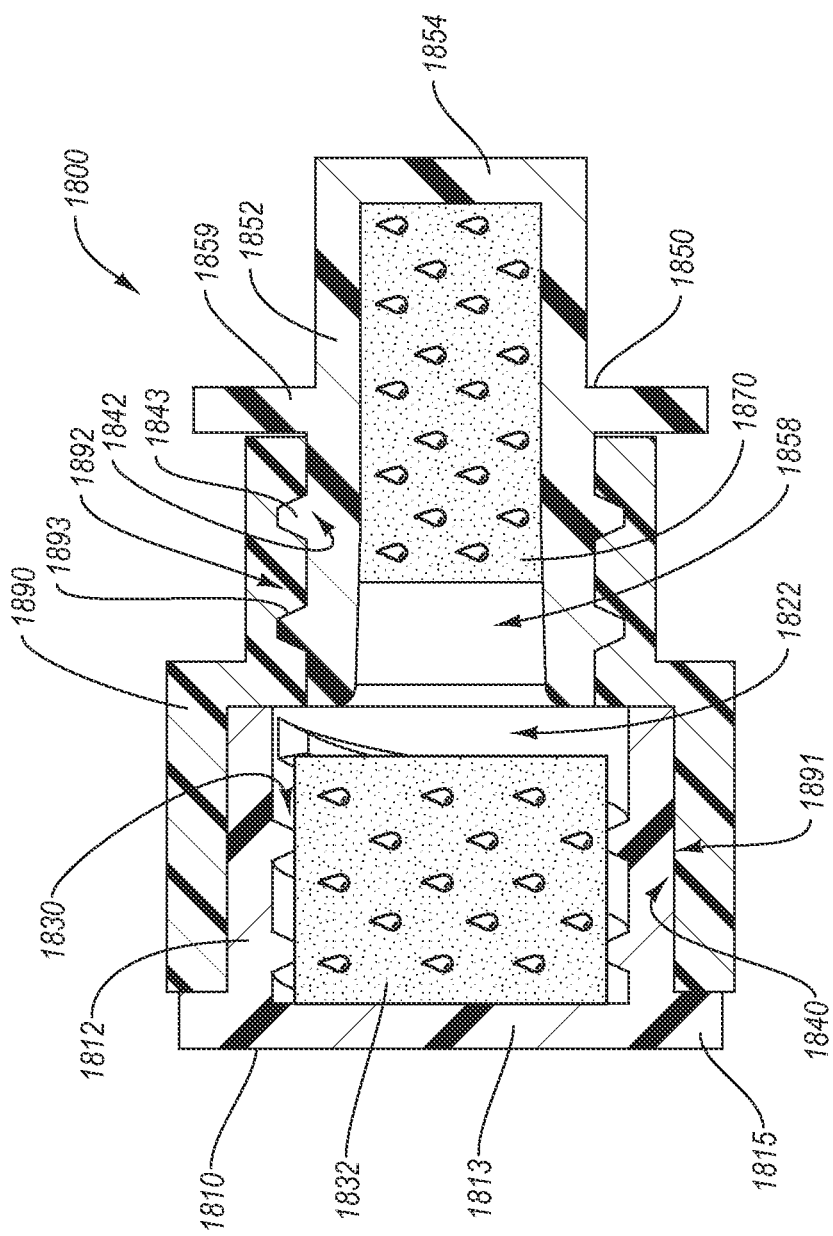
FIG. 24 is a cross-sectional view of another embodiment of an assembly that includes a pair of caps, which are attached to each other via a sleeve.
Figure 25:
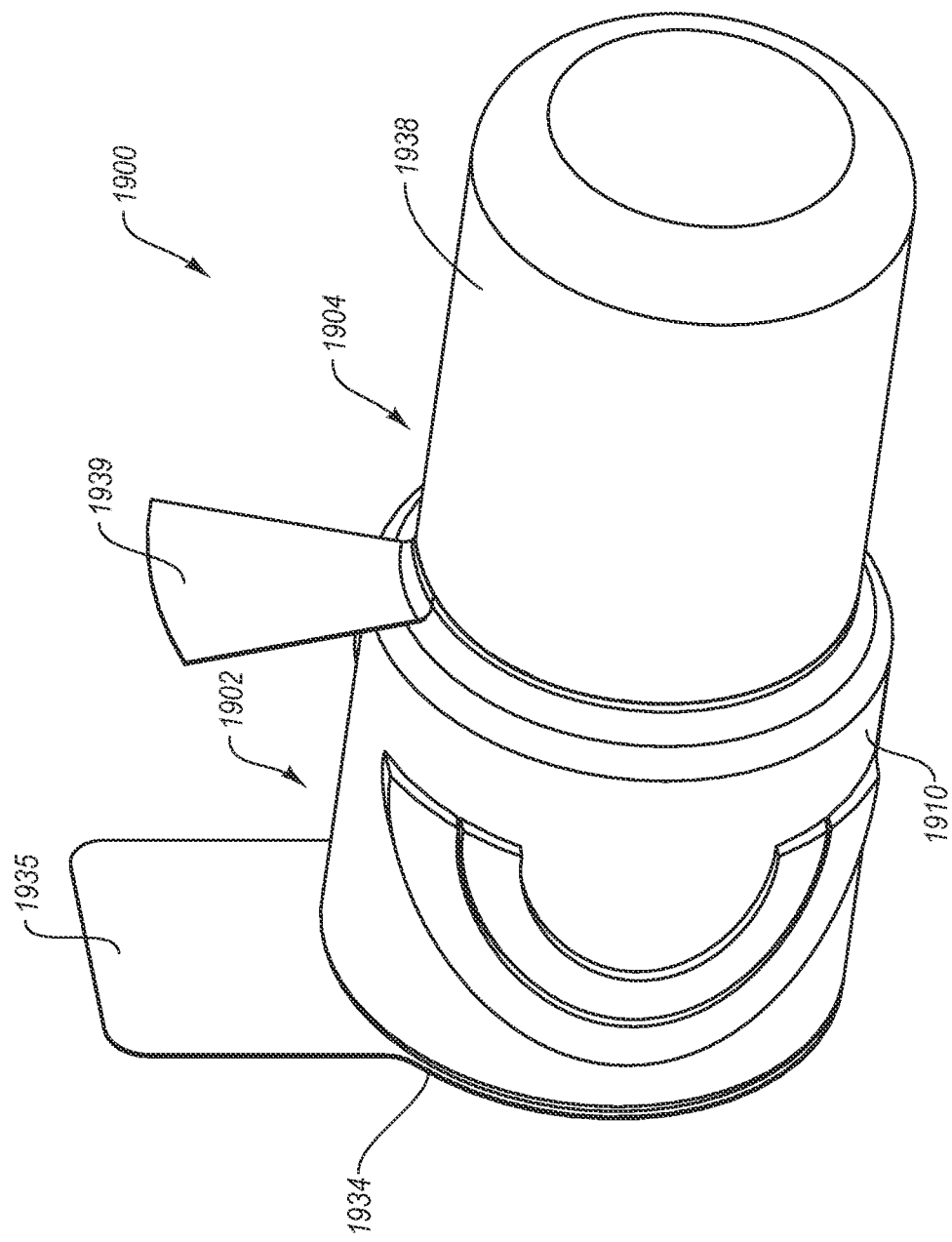
FIG. 25 is a perspective view of another embodiment of an assembly that includes two cap portions integrally connected to each other.

FIG. 24 illustrates another embodiment of an assembly 1800, which can resemble one or more of the assemblies described above in certain respects. Accordingly, like features are designated with like reference numerals, with the leading digits incremented to "18." The assembly 1800 can include a cap 1802 and cap 1804 that are coupled with each other when in a pre-use state and that can be removed from each other. In particular, the caps 1802, 1804 can be coupled with each other via a sealing mechanism. In the illustrated embodiment, the caps 1802, 1804 are coupled with each other via a sealing sleeve 1890. The caps 1802, 1804 can have open ends facing one another, and sterilization chambers 1822, 1858 of the caps 1802, 1804 can be in fluid communication with each other, when in the pre-use configuration.

The cap 1802 can include a housing 1810, which can include a sidewall 1812 and a base wall 1813. The sidewall 1812 can cooperate with the base wall 1813 to define the sterilization chamber 1822. The sterilization chamber 1822 can include a connection interface 1830, which, in the illustrated embodiment, includes threading 1831 disposed on an interior surface of the housing 1812. The connection interface 1830 can be configured to attach the cap 1802 to a medical connector in a secure yet selectively removable manner. The sterilization chamber 1822 can include a pad 1832.

An exterior surface of the sidewall 1812 can define a connection interface 1840 that is configured to couple the cap 1802 with a connection interface 1891 of the sleeve 1890. In the illustrated embodiment, the connection interfaces 1840, 1891 couple with each other via a friction-fit engagement. The friction fit can be sufficiently strong to provide a fluid-tight seal between the cap 1802 and the sleeve 1890, yet can allow the cap 1802 to be removed from the sleeve 1890 via mere manipulation by a medical practitioner (e.g., without the use of ancillary tools). The fluid-tight seal can prevent evaporative loss of antiseptic from the pad 1832 and/or can maintain the sterility of the sterilization chamber 1822. In other or further embodiments, the connection interfaces 1840, 1891 can include threading or other suitable attachment features.

In the illustrated embodiment, the base wall 1813 protrudes slightly beyond an end of the sleeve 1890, which can aid in manipulating the cap 1802 away from the sleeve 1890. In other embodiments, the base wall 1813 can protrude even further, or can include one or more protrusions or gripping features, that can aid in removing the cap 1802 from the sleeve 1890.

The cap 1802 can include a flange 1815 having an outer diameter larger than an inner diameter of the end of the sleeve 1890 that connects with the cap 1802. The flange 1815 can prevent the cap 1802 from being inserted into the sleeve 1890 too deeply. In other or further embodiments, the flange 1815 can cooperate with an end surface of the sleeve 1890 to create a liquid-tight seal. For example, in some embodiments, a sealing member, such as an "O" ring, is included between the flange 1815 and the end of the sleeve 1890 to provide the liquid-tight seal.

The cap 1804 can include a housing 1850 that includes a sidewall 1852 and a base wall 1854. The sidewall 1852 and the base wall 1854 can cooperate to define a sterilization chamber 1858, which can include a pad 1870 therein. A portion of the sidewall 1852 can define a connection interface 1842, which includes one or more threads 1843 in the illustrated embodiment. The connection interface 1842 can be configured to attach the cap 1804 to a medical connector in a secure yet selectively removable manner. Additionally, the connection interface 1842 can cooperate with a connection interface 1892 defined by the sleeve 1890 to couple the cap 1804 with the cap 1802. The connection interface 1892 can include threading 1893 that is complementary to the threading 1843. The interfaces 1842, 1892, when coupled with each other, can provide a fluid-tight seal between the cap 1804 and the sleeve 1890. In other embodiments, the connection interfaces 1842, 1890 can instead define a friction-fit seal, such as that provided by the illustrated embodiment of the connection interfaces 1840, 1891 described above. In still other or further embodiments, a flange 1859 defined by the housing 1850 can cooperate with an end surface of the sleeve 1890 to create a liquid-tight seal, which can prevent evaporative loss of antiseptic from the pad 1870 and/or maintain the sterility of the sterilization chamber 1858. For example, in some embodiments, a sealing member, such as an "O" ring, is included between the flange 1859 and the end of the sleeve 1890 to provide the liquid-tight seal.

Features, usage, and operation of the assembly 1800 can resemble that of one or more of the assemblies described above. For example, when the assembly 1800 is in the pre-use condition, each sterilization chamber 1822, 1858 can be defined by a separate housing 1812, 1850. Likewise, the caps 1802, 1804 can be coaxial with each other, and the open ends of the caps 1802, 1804 can face in opposite directions (e.g., towards each other). In the illustrated embodiment, each of the pads 1832, 1870 is in an uncompressed or expanded state when the sterilization chamber 1822, 1858 in which it is housed is in a pre-use, sealed condition.

However, certain differences can exist. For example, in the illustrated embodiment, the sterilization chambers 1822, 1858 are in fluid communication with each other when the caps 1802, 1804 are in the pre-use state. Moreover, in the illustrated embodiment, no portion of the housing 1850 of the cap 1804 is received within, or nested within, any portion of the housing 1810 of the cap 1802.

FIGS. 25-29 illustrate another embodiment of an assembly 1900, which can resemble one or more of the assemblies described above in certain respects. Accordingly, like features are designated with like reference numerals, with the leading digits incremented to "19." As shown, for example, FIGS. 25 and 26, the assembly 1900 can include a male cap portion or cap 1902 and a female cap portion or cap 1904 that are integrally formed or otherwise permanently attached with each other. For example, the caps 1902, 1904 can include a single, integrally molded housing 1910. The cap 1902 can be configured to couple with a female connector, and the cap 1904 can be configured to couple with a male connector. In the illustrated embodiment, the caps 1902, 1904 are in a coaxial arrangement. As shown, for example, in FIGS. 26 and 28, the assembly 1900 can include a pad 1970 that is received within one or more of the caps 1902, 1904. As shown, for example, in FIGS. 25 and 26, each cap 1902, 1904 can be sealed shut in the pre-use configuration via a separate cover 1934, 1938, respectively. Each cover 1934, 1938 can include a tab 1935, 1939, respectively, that can aid in removal of the cover.

Figure 29:
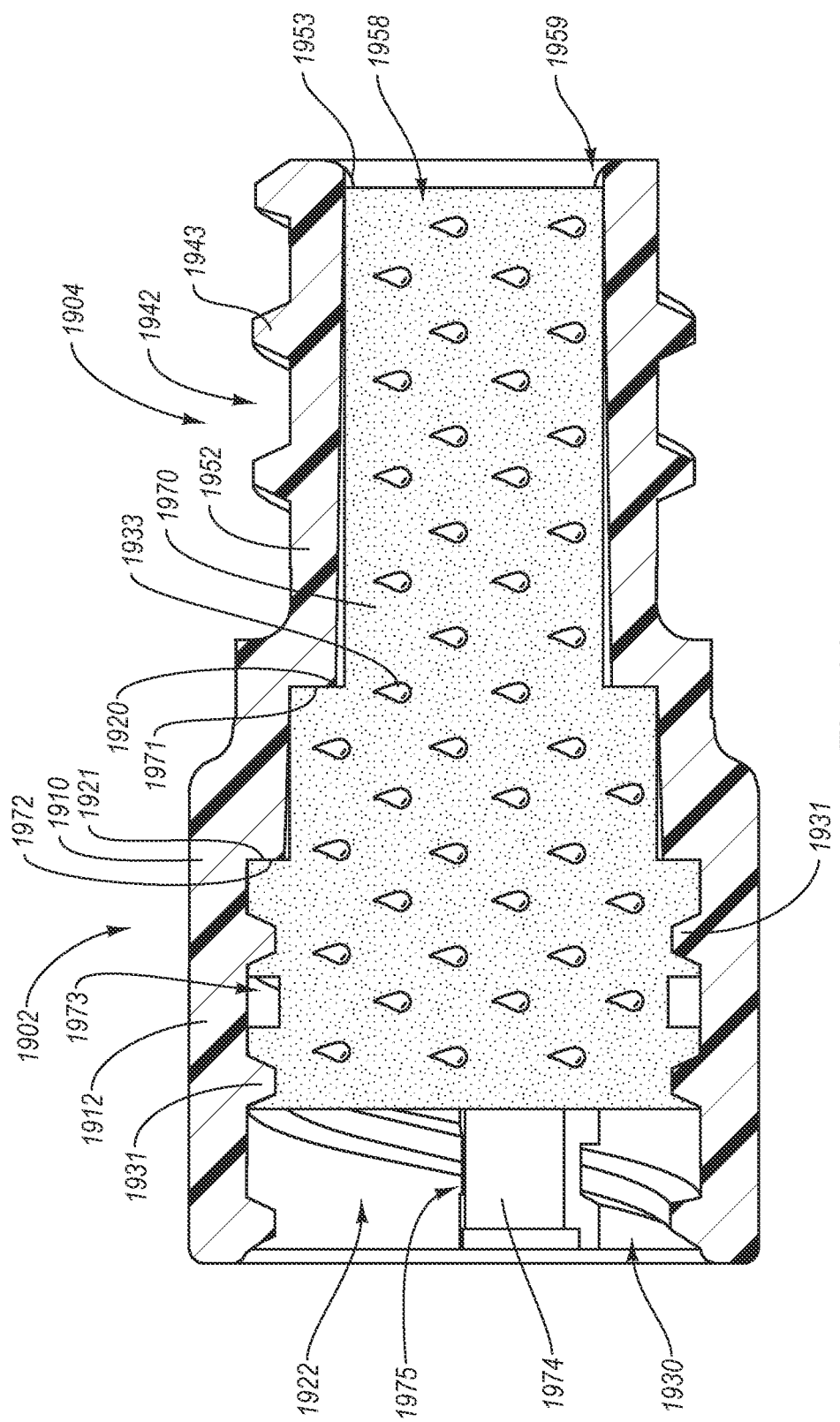
FIG. 29 is a cross-sectional view of the assembly of FIG. 28 taken along the view line 29-29.

With continued reference to FIGS. 25-29, the housing 1910 can define at least a portion of each of the caps 1902, 1904. The housing 1910 includes a first sidewall 1912 that defines a first sterilization chamber 1922 and includes a second sidewall 1952 that defines a second sterilization chamber 1958. As shown in FIG. 29, the first sidewall 1912 can define larger inner and outer diameters than those defined by the second sidewall 1952. The housing 1910 can transition from the first sidewall 1912 and the first sterilization chamber 1922 to the second sidewall 1952 and the second sterilization chamber 1958 at a constriction or abutment 1920. The housing 1910 can be substantially hollow such that the first and second sterilization chambers 1922, 1958 are in fluid communication with each other. The housing 1910 can define another abutment 1921, which is discussed further below.

Figure 26:
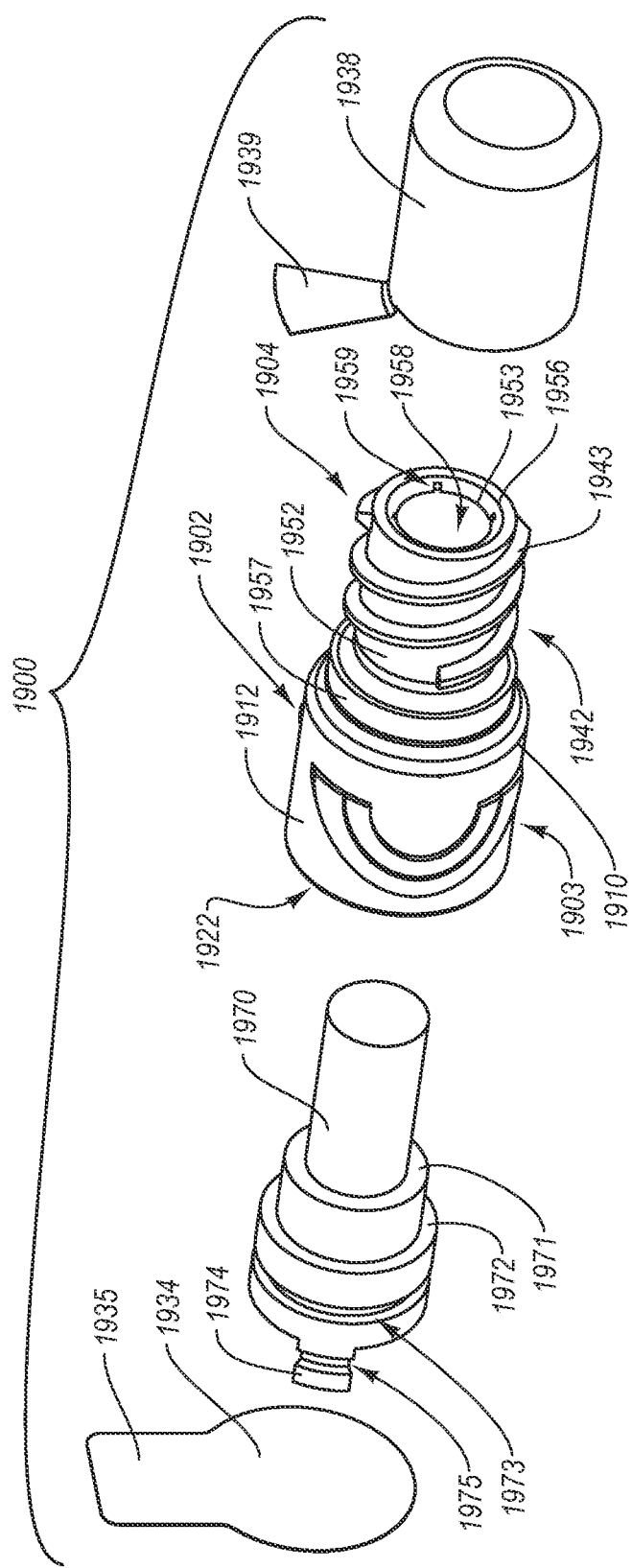
FIG. 26 is an exploded perspective view of the assembly of FIG. 25.

As shown in FIGS. 26, 28, and 29, the male cap 1902 can include a connection interface 1930 that is configured to couple with a connection interface of a medical connector, such as a needleless injection site. The connection interface 1930 can include threading 1931, which can be disposed at an interior of the sidewall 1912. In some embodiments, the male cap 1902 includes one or more gripping features 1903 at an exterior surface of the sidewall 1912. In the illustrated embodiment, the gripping features 1903 are raised areas. In other embodiments, the gripping features 1903 can include depressed areas. The gripping features 1903 can be formed in the shape of a company logo or any other suitable shape.

As shown in FIGS. 26, 27, and 29, the female cap 1904 can include a connection interface 1942 that is configured to couple with a connection interface of a medical connector, such as a medical attachment having a male luer. The connection interface 1942 can include threading 1943, which can be disposed at an exterior surface of the sidewall 1952. The cap 1904 can include one or more vents 1959, which can be located at an end of the sidewall 1952. The one or more vents can also extend along the length of sidewall 1952. In the illustrated embodiment, a constriction, rim, or lip 1953 projects radially inwardly at the end of the sidewall 1952, which can aid in maintaining the pad 1970 within the cap 1904. In particular, the lip 1953 can define a smaller inner diameter than an outer diameter of the pad 1970 (see FIG. 29). The vents 1959 can comprise notches in the lip 1953. The illustrated embodiment includes four vents 1959, although more or fewer vents are possible.

With reference to FIG. 26, the pad 1970 can define a shape generally resembling a series of tiered cylinders. A rim 1971 can extend transversely, or radially outwardly, from a cylinder that has the smallest diameter. Another rim 1972 can extend transversely from a cylinder having an intermediate diameter. The largest cylinder can have a recess 1973 disposed therein. In certain embodiments, such as the illustrated embodiment, one or more extensions 1974 protrude from an end of the pad 1970 in a longitudinal direction. Each extension 1974 can include a groove 1975 therein, as discussed further below. In other embodiments, the one or more extensions 1974 are omitted.

With reference to FIG. 29, the pad 1970 can be secured within the housing 1910 in any suitable manner, and thus can resist translational movement in either direction that would cause the pad 1970 to exit the housing 1910 from either open end of the housing. For example, in the illustrated embodiment, interaction of the threads 1931 with a left end of the pad 1970 can prevent the pad 1970 from moving out of the housing 1910 in a leftward direction as a portion of a medical connector (e.g., a male luer connector) is inserted into the housing 1910 from the right. As shown in FIG. 29, some portions of the pad 1970 can be compressed by the threads 1931, whereas the grooves 1975 of the extensions 1974 can accommodate the threads 1931. The enlarged tiered sections of the pad 1970, and the resultant interaction of the rims 1971, 1972 with the abutments 1920, 1921, respectively, can prevent the pad 1970 from moving out of the housing 1910 in the rightward direction as a portion of a medical connector (e.g., a needleless injection site) is advanced into the housing 1920 from the left. In other or further embodiments, the pad 1970 can be adhered to the housing 1910.

With reference to FIGS. 26 and 27, the cover 1938 can be secured to the housing 1910 in any suitable manner. For example, in some embodiments, an end of the cover 1938 is adhered or otherwise sealed to a sealing surface 1956 at an end of the sidewall 1952 so as to provide a hermetic seal. A side portion of the cover 1938 thus can cover the connection interface 1942 of the cap 1904. In other or further embodiments, a lower circumferential edge of the cover 1938 can be adhered or otherwise sealed to a sealing surface 1957 at a base end of the sidewall 1952 so as to provide a hermetic seal. With reference to FIGS. 26 and 28, the cover 1934 can be adhered or otherwise sealed to a sealing surface 1916 at an end of the sidewall 1912 of the housing 1910.

Figure 30:
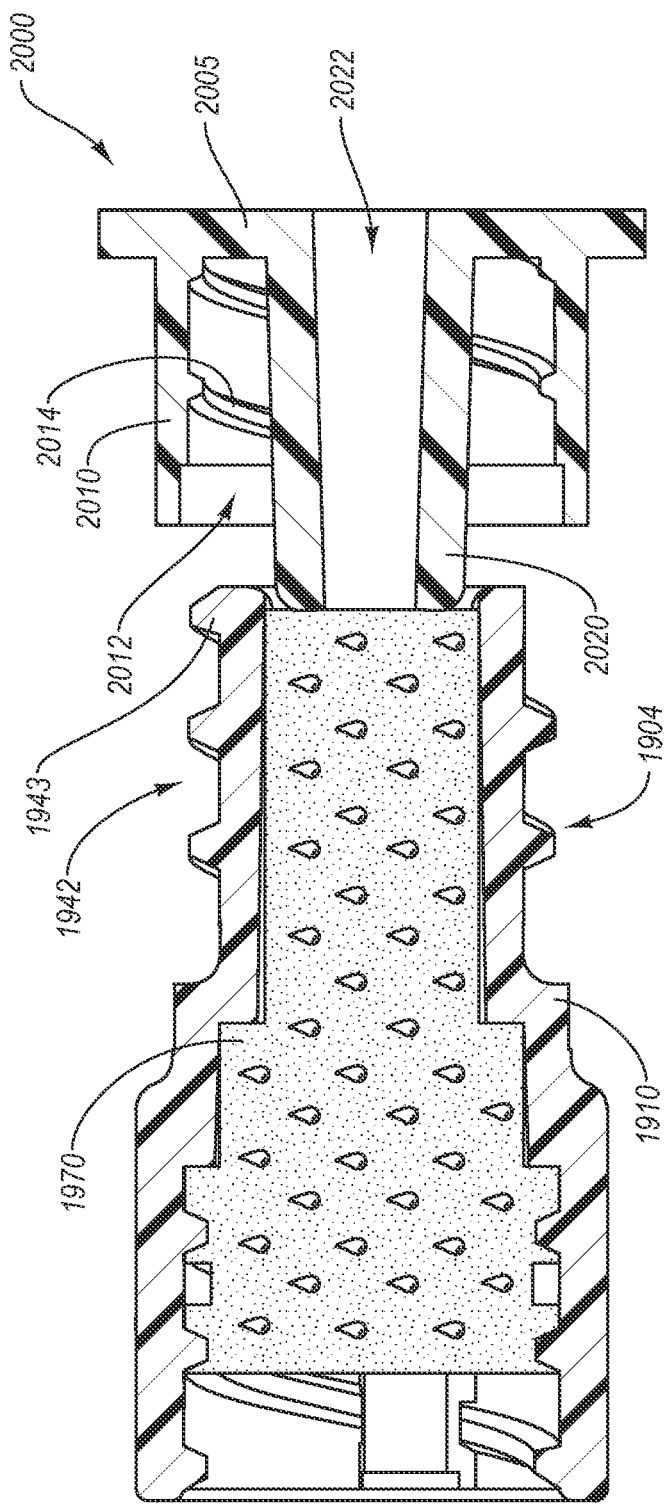
FIG. 30 is a cross-sectional view of the assembly of FIG. 25 showing an early stage of coupling a cap portion of the assembly with a medical connector that has a male luer.

FIG. 30 illustrates an early stage of the coupling of a medical connector 2000 with the cap 1904. The medical connector 2000 can include a housing 2005 that complies with ISO standards (e.g., ISO 594-1:1986 and ISO 594-2: 1998). The housing 2005 can include a skirt 2010 that defines a connection interface 2012, which itself can include threading 2014. The housing 2005 can also include a male luer 2020, which can define a fluid passageway 2022.

In the illustrated embodiment, a tip of the male luer 2020 can contact an end surface of the pad 1970 prior to engagement of the connection interfaces 1942, 2012 (e.g., the threadings 1943, 2014) with each other. Accordingly, some compression of the pad 1970 may occur without assistance from the connection interfaces 1942, 2012. In other embodiments, the connection interfaces 1942, 2012 may engage one another prior to contact being made between the tip of the male luer 2020 and the end surface of the pad 1970, such as may occur when the pad 1970 is more recessed within the housing 1910 and/or the skirt 2010 and its connection interface 2012 are longer. In either case, in some embodiments, the connection interfaces 1942, 2012 can assist in the compression of the pad 1970. The desired antiseptic concentration level of the pad 1970 is determined by the volume required to fully coat and sterilize the medical connector 2000, while taking into consideration the evaporative loss that may occur during the shelf life of cap 1904.

Figure 31:
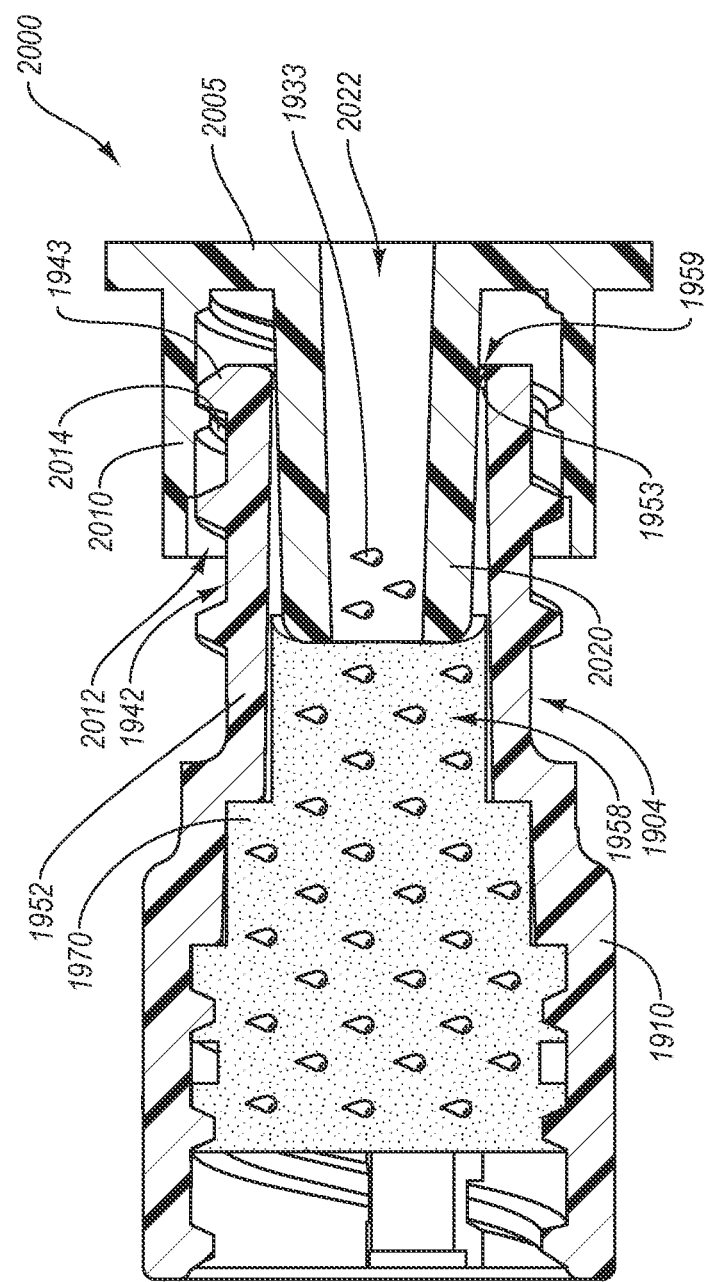
FIG. 31 is a cross-sectional view of the assembly of FIG. 25 showing a late stage of coupling the cap portion of the assembly with the medical connector that has a male luer.

FIG. 31 illustrates a later stage of the coupling of the medical connector 2000 with the cap 1904. As the male luer 2020 is advanced into the sterilization chamber 1958 of the cap 1904, it compresses the pad 1970 and causes antiseptic 1933 to egress therefrom. The pad 1970 can remain relatively fixed, rotationally, while the male luer 2020 is rotated and advanced further into the chamber 1958, which can effect a rubbing or scrubbing of the tip of the luer 2020, particularly as increased compression of the pad 1970 provides an increased force of the pad 1970 against the tip. The released antiseptic can fill an opening or volume of space between the sidewall 1952 of the housing 1910 and an outer surface of the male luer 2020, and can thereby sterilize the outer surface of the male luer 2020. Additionally, in the illustrated embodiment, the fluid passageway 2022 of the male luer 2020 is open such that antiseptic fluid 1933 may enter into it.

In certain embodiments, a seal can form between the lip 1953 and the male luer 2020 when the luer 2020 is advanced sufficiently far into the chamber 1958. The seal thus formed can be an interrupted seal, such that the seal is formed only at those regions where the luer 2020 and the lip 1953 are in contact with each other. Antiseptic 1933 can be permitted to exit from the chamber 1958 via the vents 1959. In some embodiments, the vents 1959 are sufficiently large to permit antiseptic 1933 to exit from the chamber 1958 freely once the antiseptic 1933 has been expelled from the pad 1970. Antiseptic 1933 that exits from the chamber 1958 through the vents 1959 can sterilize portions of the male luer 2020 that are proximal of the lip 1953.

In other embodiments, the vents 1959 are sufficiently small to prevent antiseptic 1953 from exiting from the chamber 1958 when a pressure within the chamber 1958 is the same or approximately the same as a pressure outside of the chamber 1958 (e.g., atmospheric pressure), and yet are sufficiently large to permit antiseptic 1933 to exit the chamber 1958 when the pressure within the chamber 1958 is significantly greater than the pressure outside of the chamber 1958, such as may result when the luer 2020 is being advanced deeper within the chamber 1958. The vents 1959 thus can permit selective egress of the antiseptic 1933 to aid in achieving the desired positioning of the male luer 2020, yet can maintain the antiseptic 1933 within the chamber 1958 so as to bathe a portion of the male luer 2020 once the male luer 2020 is positioned as desired. In still other embodiments, a fluid-tight seal is formed between the lip 1953 and the male luer 2020.

In certain embodiments, the pad 1970 may be recessed within the chamber 1958 to a greater degree when in the uncompressed state (e.g., when in the state shown in FIG. 30). Moreover, the threads 2014 of the connection interface 2012 and the threads 1943 of the connection interface 1942 can permit the antiseptic 1933 to pass through them, so as to provide additional venting of the chamber 1958. For example, threaded connection interfaces 2012, 1942 can permit antiseptic 1933 that has exited from the chamber 1958 to spiral about an outer surface of the second sidewall 1952 in a distal direction.

Figure 32:
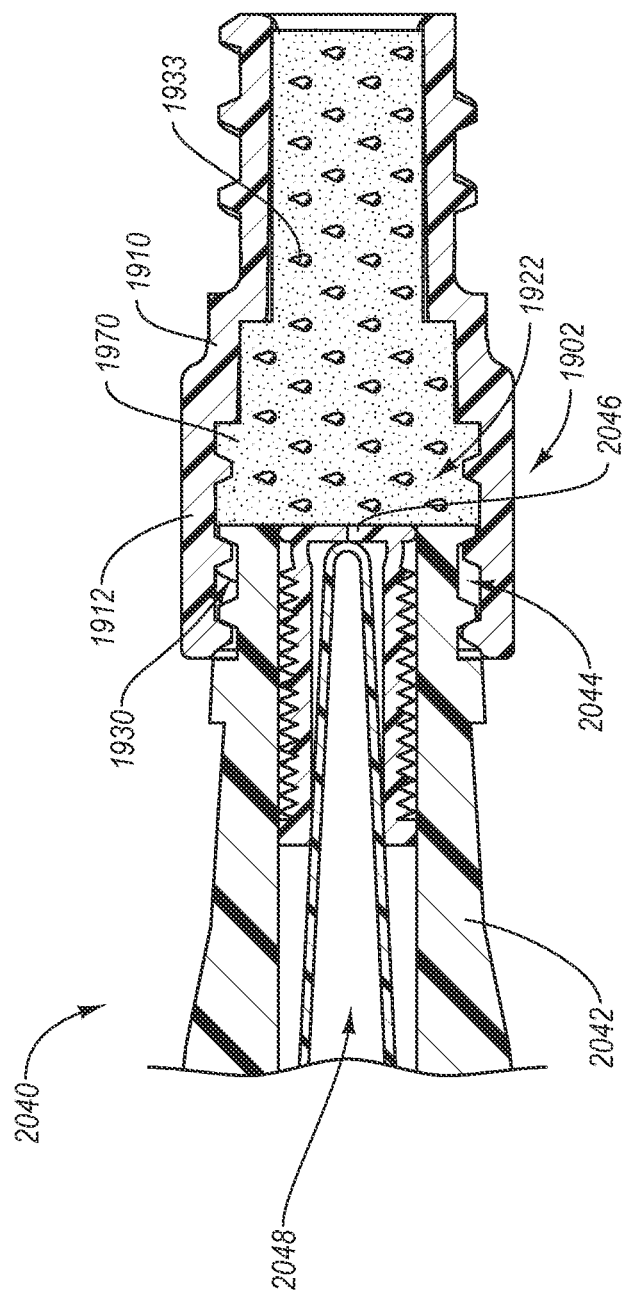
FIG. 32 is a cross-sectional view of the assembly of FIG. 25 showing a late stage of coupling the other cap portion of the assembly with a first embodiment of a needleless injection site.
Figure 33:
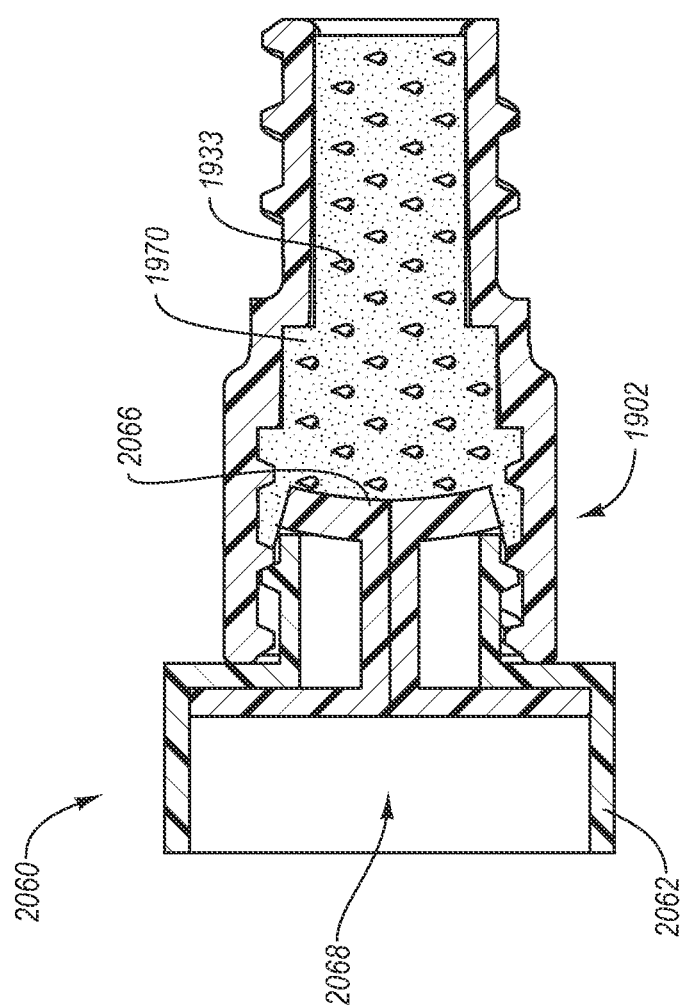
FIG. 33 is a cross-sectional view of the assembly of FIG. 25 showing a late stage of coupling the other cap portion of the assembly with a second embodiment of a needleless injection site.
Figure 34:
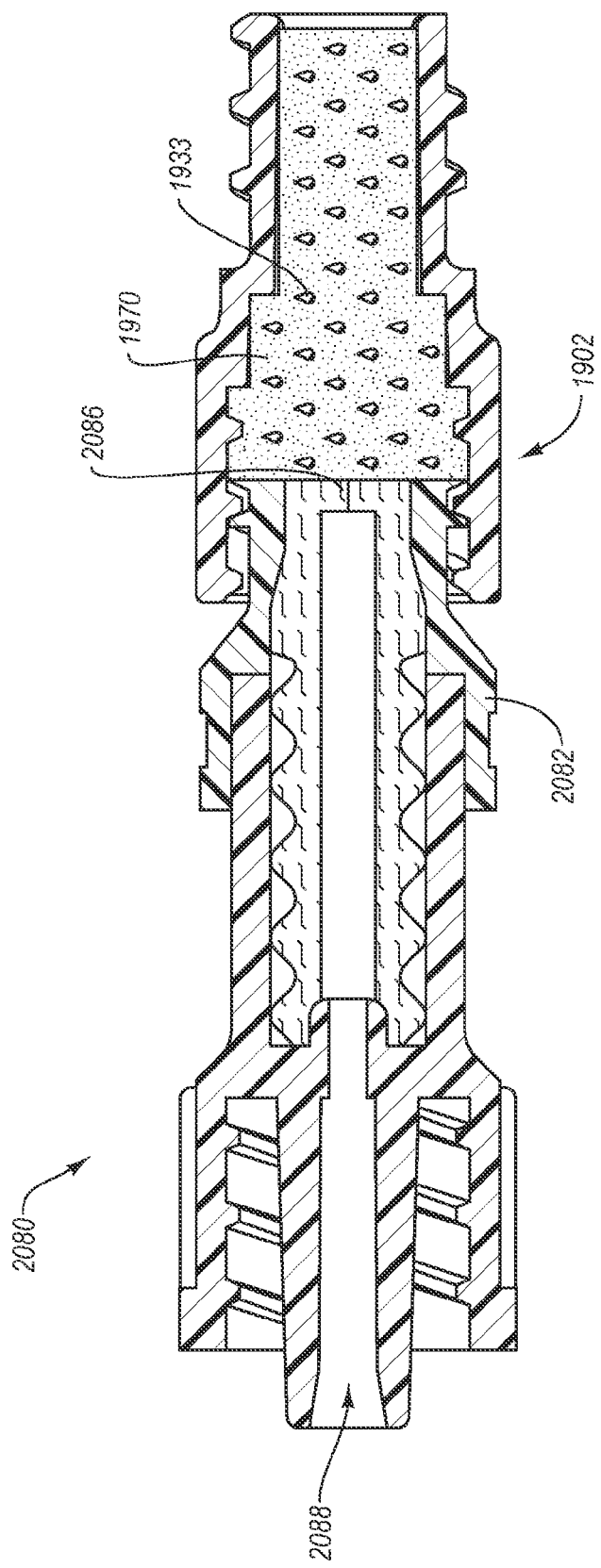
FIG. 34 is a cross-sectional view of the assembly of FIG. 25 showing a late stage of coupling the other cap portion of the assembly with a third embodiment of a needleless injection site.

Each of FIGS. 32-34 illustrates the cap 1902 coupled with a separate needleless injection site 2040, 2060, 2080. As with other caps disclosed herein, the cap 1902 can be versatile so as to couple with a variety of different types of medical connectors in a secure fashion that sterilizes each type of medical connector. As can be seen in each of FIGS. 32-34, coupling of the needleless injection sites 2040, 2060, 2080 with the cap 1902 can effect compression of one end of the pad 1970 in a manner similar to that described above with respect to compression of the other end of the pad 1970. Compression of the pad 1970 and rotation of the needleless injection site 2040, 2060, 2080 can effect rubbing, swabbing, or scrubbing of the needleless injection site and sterilization thereof via the antiseptic 1933.

With reference to FIG. 32, the needleless injection site 2040 can comprise a Clave® port available from ICU Medical, Inc. The needleless injection site 2040 can include a housing 2042 that defines a connection interface 2044. The needleless injection site 2040 can further include an elastomeric seal 2046, which is shown in a closed configuration in which fluid access is not permitted into a fluid passageway 2048. Small crevices can exist between the housing 2042 and the elastomeric seal 2046 at an end of the needleless injection site 2040 that is inserted into sterilization chamber 1922. As the connection interface 2044 cooperates with the connection interface 1930 defined by the sidewall 1912 to draw the tip of the needleless injection site 2040 into the sterilization chamber 1922, the pad 1970 can be compressed so as to generally conform to the crevices. Compression of the pad 1970 likewise can expel antiseptic 1933, which, in some instances, can fill in portions of the crevices that the pad 1970 may not be able to contact directly. As the pad 1970 is compressed, the seal 2046 can remain closed so as to prevent antiseptic 1933 from entering the fluid passageway 2048. With reference again to FIG. 29, if present, the one or more extensions 1974, due to their positioning over the threads 1031, additionally can rub or scrub the side surfaces of the needleless injection site 2040. Thus, a thorough rubbing and sterilization of the needleless injection site 2040 can be accomplished via the cap 1902, and the performance of the cap 1902 in this regard can exceed that achieved via standard swabbing protocols, and can be less susceptible to human error.

With reference to FIG. 33, the needleless injection site 2060 can comprise a Q-Syte® port available from Becton, Dickinson and Company. The needleless injection site 2060 can include a housing 2062 and an elastomeric seal 2066, which is shown in a closed configuration in which fluid access is not permitted into a fluid passageway 2068. As with the needleless injection site 2040, small crevices can exist between the housing 2062 and the elastomeric seal 2066. However, the crevices can exist at a side portion of the needleless injection site 2060, rather than at its tip. Nevertheless, as the needleless injection site 2060 is advanced into the cap 1902, the pad 1970 can be compressed so as to generally conform to these differently shaped crevices. Compression of the pad 1970 likewise can expel antiseptic 1933, which, in some instances, can fill in portions of the crevices that the pad 1970 may not be able to contact directly. The seal 2066 can be maintained in the closed position during the coupling procedure so as to prevent any of the antiseptic 1933 from entering the fluid passageway 2068.

With reference to FIG. 34, the needleless injection site 2080 can comprise a SmartSite® port available from Cardinal Health, Inc. The needleless injection site 2080 can include a housing 2082 and an elastomeric seal 2086, which is shown in a closed configuration in which fluid access is not permitted into a fluid passageway 2088. As with the needleless injection sites 2040, 2060, small crevices can exist between the housing 2082 and the elastomeric seal 2086. However, these crevices can be in yet different positions than those of the needleless injection sites 2040, 2060. Nevertheless, as the needleless injection site 2080 is advanced into the cap 1902, the pad 1970 can be compressed so as to generally conform to these differently shaped crevices. Compression of the pad 1970 likewise can expel antiseptic 1933, which, in some instances, can fill in portions of the crevices that the pad 1970 may not be able to contact directly. The seal 2086 can be maintained in the closed position during the coupling procedure so as to prevent any of the antiseptic 1933 from entering the fluid passageway 2088. Additionally, each of the needleless injection sites 2040, 2060, 2080 may advance into the cap 1902 by different amounts. The cap 1902 thus can be adaptable and versatile. Additional, non-limiting examples of needleless injection sites with which the cap 1902 can selectively couple include the Clearlink® Site available from Baxter and the InVision-Plus® available from Rymed.

Features, usage, and operation of the assembly 1900 can resemble that of one or more of the assemblies described above. For example, in the illustrated embodiment, the pad 1970 is in an uncompressed or expanded state when the sterilization chambers 1922, 1958 in which it is housed are in a pre-use, sealed condition. Additionally, the caps 1902, 1904 are coaxial with each other with open ends that face in opposite directions. Likewise, the caps 1902, 1904 are connected to each other when the assembly 1900 is in a pre-use state.

However, certain differences can exist. For example, in the illustrated embodiment, the caps 1902, 1904 cannot be removed from each other. Moreover, the assembly 1900 includes a single pad 1970 that is used in both caps 1902, 1904. Although not shown in the drawings, it is understood that each cap 1902, 1904 can be coupled with a separate medical connector such that the pad 1970 is compressed from both ends when the caps 1902, 1904 are in a coupled state.

Figure 35:
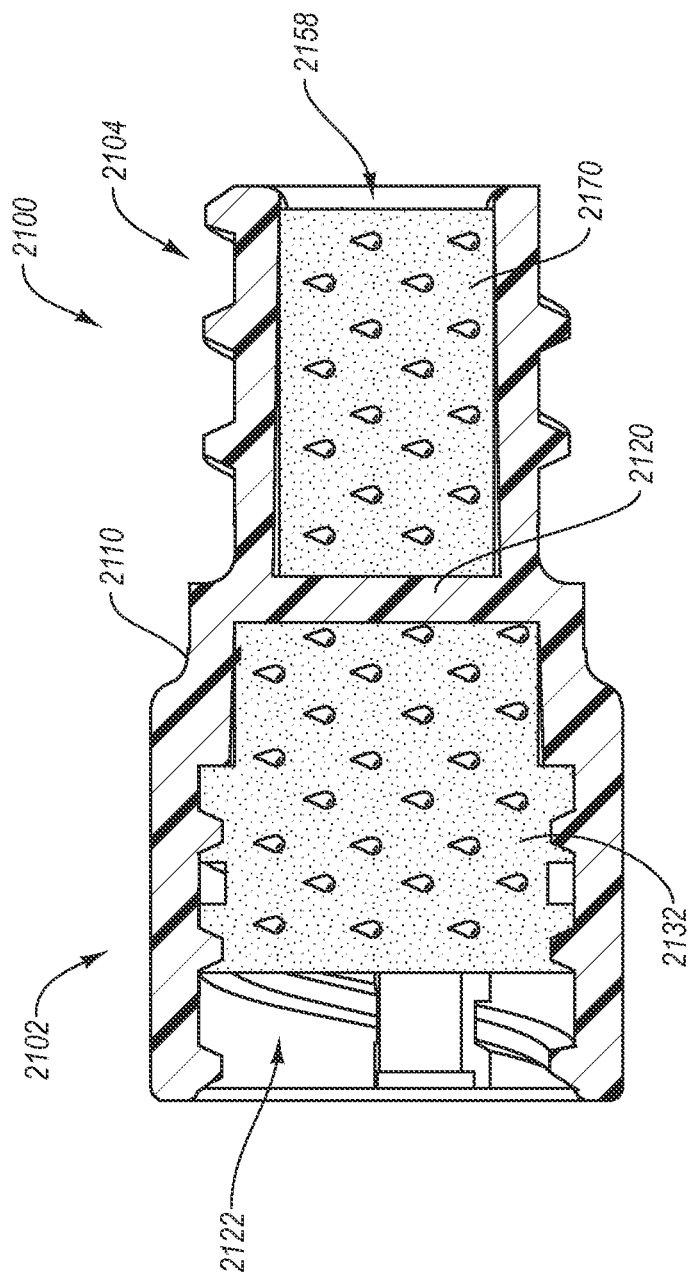
FIG. 35 is a cross-sectional view of another embodiment of an assembly that includes two cap portions integrally connected to each other, with covers removed from the assembly.

FIG. 35 illustrates another embodiment of an assembly 2100, which can resemble one or more of the assemblies described above, particularly the assembly 1900, in certain respects. Accordingly, like features are designated with like reference numerals, with the leading digits incremented to "21." The assembly 2100 can include caps 2102, 2104, such as the caps 1902, 1904, that are fixedly, permanently, or integrally connected with each other. Covers such as the covers 1934, 1938, which are not shown in FIG. 35, can be used with the caps 2102, 2104. The assembly 2100 can include a single housing 2110 that defines two sterilization chambers 2122, 2158. The housing 2110 can include a partition 2120 that separates the sterilization chambers 2122, 2158 from each other such that the chambers 2122, 2158 are fluidly separated from one another. Each chamber 2122, 2158 can include a separate pad 2132, 2170 therein.

The caps described herein can be formed of, or coated with various colored materials or coatings. In some embodiments, the caps each include the same color. In other embodiments, the caps include different colors. Coloring the caps can, in some instances, provide advantages, such as ready identification of the type of cap, ready matching of a particularly colored cap with a particular type of medical connector, and the like.

The foregoing disclosure recites various embodiments that include systems configured for use with a pair of separated medical connectors. Examples of first means for coupling a male cap with a first medical connector include the connection interfaces 1042, 1142, 1342, 1542, 1842, 1942 of the caps 1004, 1104, 1304, 1504, 1804, and 1904. Examples of first means for sterilizing a male luer of a first medical connector include the pads 1070, 1170, 1370, 1570, 1870, 2170. Examples of second means for coupling the female cap with a second medical connector include the connection interfaces 1030, 1130, 1530, 1830, 1930 of the caps 1002, 1102, 1502, 1802, 1902. Examples of second means for sterilizing at least a portion of a second medical connector include the pads 1032, 1132, 1332, 1532, 1832, 2132. Examples of means for coupling the male and female caps in a pre-use configuration include the connection interfaces 1040 and 1042; 1140 and 1180; 1240 and 1280; 1340 and 1380; 1440 and 1480; 1540 and 1580; and 1840, 1891, 1842, and 1892.

It will be understood by those having skill in the art that many changes may be made to the details of the above-described embodiments without departing from the underlying principles presented herein. For example, any suitable combination of features of the various embodiments of assemblies described above is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

It should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. §112 ¶6. It will be apparent to those having skill in the art that changes may be made to the details of the above-described embodiments without departing from the underlying principles of the invention.

What is claimed is:

1. A system of medical luer connector caps comprising:
   at least two disinfecting caps, each including a receiving portion having (i) a chamber defining an opening in which a medical tubing connector can be received, (ii) an exterior surface extending around the opening for receiving a cover, (iii) a means for engaging threads of luer connectors; and
   a cover extending over and solely in contact with the exterior surface of each of the at least two disinfecting caps, so as to seal the chambers of the at least two disinfecting caps.

2. A system according to claim 1, wherein the means for engaging threads of at least one of the disinfecting caps is disposed on an exterior wall of the cap so as to engage a male luer connector.

3. A system according to claim 2, wherein the means for engaging threads includes a helical thread.

4. A system according to claim 1, wherein the means for engaging threads of at least one of the disinfecting caps is disposed in the chamber of the cap so as to engage a female luer connector.

5. A system according to claim 4, wherein the means for engaging threads includes a helical thread.

6. A system according to claim 1 wherein the cover comprises an adhesive.

7. A system according to claim 1 wherein the cover comprises an impervious pliable material.

8. A system according to claim 7 wherein the material is a foil or a plastic.

9. A system according to claim 1 wherein each of the at least two caps further comprises a connection interface.

10. A system according to claim 1 wherein the at least two caps are connected to one-another by an interlocking means.

11. A system according to claim 1 wherein at least one of the cap comprises a slot for engaging a protrusion of another of the at least two caps.

12. A system according to claim 1 wherein each of the caps further comprise a gripping portion.

13. A system according to claim 12 wherein each of the caps are connected to one-another at their respective gripping portion.

14. A system according to claim 1 wherein the system further comprise an antiseptic agent.

15. A system according to claim 14 wherein the system further comprise an absorbent pad.

16. A system of medical luer connector caps comprising:
   a first disinfecting cap, including a first receiving portion having (i) a first chamber defining a first opening in which a medical tubing connector can be received, (ii) a first exterior surface extending around the first opening for receiving a cover, (iii) first means for engaging threads of luer connectors;
   a second disinfecting cap, including a second receiving portion having (i) a second chamber defining a second opening in which a medical tubing connector can be received, (ii) a second exterior surface extending around the second opening for receiving a cover, (iii) second means for engaging threads of luer connectors; and
   a cover extending over and solely in contact with the first and second exterior surfaces, so as to seal the first and second chambers.

* * * * *